United States Patent [19]

Grossman et al.

[11] Patent Number: 5,624,800
[45] Date of Patent: *Apr. 29, 1997

[54] METHOD OF DNA SEQUENCING EMPLOYING A MIXED DNA-POLYMER CHAIN PROBE

[75] Inventors: Paul D. Grossman, Burlingame; Steven Fung, Palo Alto; Steven M. Menchen, Fremont; Sam L. Woo, Redwood City; Emily S. Winn-Deen, Foster City, all of Calif.

[73] Assignee: The Perkin-Elmer Corporation, Foster City, Calif.

[*] Notice: The term of this patent shall not extend beyond the expiration date of Pat. No. 5,580,732.

[21] Appl. No.: 447,174

[22] Filed: May 19, 1995

Related U.S. Application Data

[63] Continuation of Ser. No. 296,880, Aug. 26, 1994, which is a continuation of Ser. No. 973,118, Nov. 6, 1992, abandoned, which is a continuation-in-part of Ser. No. 866,018, Apr. 7, 1992, Pat. No. 5,470,705, and Ser. No. 862,642, Apr. 3, 1992, abandoned.

[51] Int. Cl.$^6$ .............................. C12Q 1/68; C12P 19/34
[52] U.S. Cl. .................................. 435/6; 435/91.1
[58] Field of Search ............................ 435/91.1, 810, 435/6; 436/94

[56] References Cited

U.S. PATENT DOCUMENTS

| | | |
|---|---|---|
| 4,879,214 | 11/1989 | Kornher et al. . |
| 5,108,568 | 4/1992 | Van Alstine . |
| 5,171,534 | 12/1992 | Smith et al. . |
| 5,514,543 | 5/1996 | Grossman et al. ................... 435/6 |

OTHER PUBLICATIONS

J.Noolandi Electrophoresis 13:394–395 (1992) A new concept for sequencing DNA by capillary electrophoresis.

K.L.Livak et al. Nucleic Acids Research 20(18): 4831–4837 (1992) Detection of single base differences using biotinylated nucleotides with very long linker arms.

J.S.Kornher et al. Nucleic Acids Research 17(19): 7779–7784 (1989) Mutation detection using nucleotide analogs that alter electrophoretic mobility.

P.Mayer et al. Analytical Chemistry 66: 1777–1780 (1994) Theory of DNA sequencing using free solution electrophoresis of protein–DNA complexes.

W.Muller et al Nucleic Acids Research 9(1): 95–119 (1981) Polyethylene glycol derivatives of base and sequence specific DNA ligands: DNA interaction and application for base specific separation of DNA fragments by gel electrophoresis.

R.L.Cunico et al. Journal of Chromatography 559: 467–477 (1991) Characterization of polyethylene glycol modified proteins using charge reversed capillary electrophoresis.

*Primary Examiner*—Kenneth R. Horlick
*Attorney, Agent, or Firm*—Paul D. Grossman; Peter J. Dehlinger; Stephen C. Macevicz

[57] ABSTRACT

Method and composition for detecting one or more selected polynucleotide regions in a target polynucleotide. In the method, a mixture of sequence-specific probes are reacted with the target polynucleotide under hybridization conditions, and the hybridized probes are treated to selectively modify those probes which are bound to the target polynucleotide in a base-specific manner. The resulting labeled probes include a polymer chain which imparts to each different-sequence probe, a distinctive ratio of charge/translational frictional drag, and a detectable label. The labeled probes are fractionated by electrophoresis in a non-sieving matrix, and the presence of one or more selected sequences in the target polynucleotide are detected according to the observed electrophoretic migration rates of the labeled probes in a non-sieving medium.

7 Claims, 15 Drawing Sheets

↓ PROBE COMPOSITION
↓ ANNEAL

LIGASE ↓

↓ DENATURE

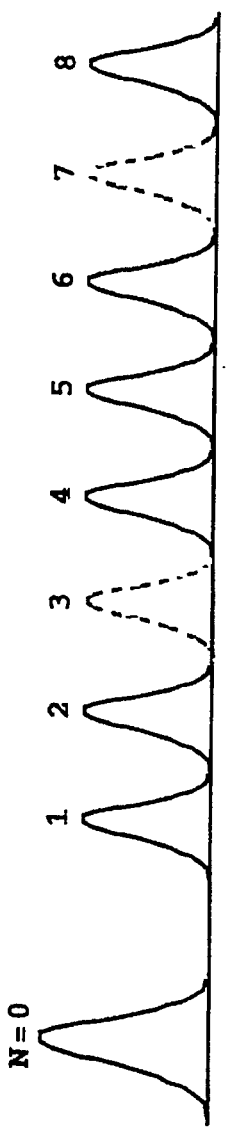
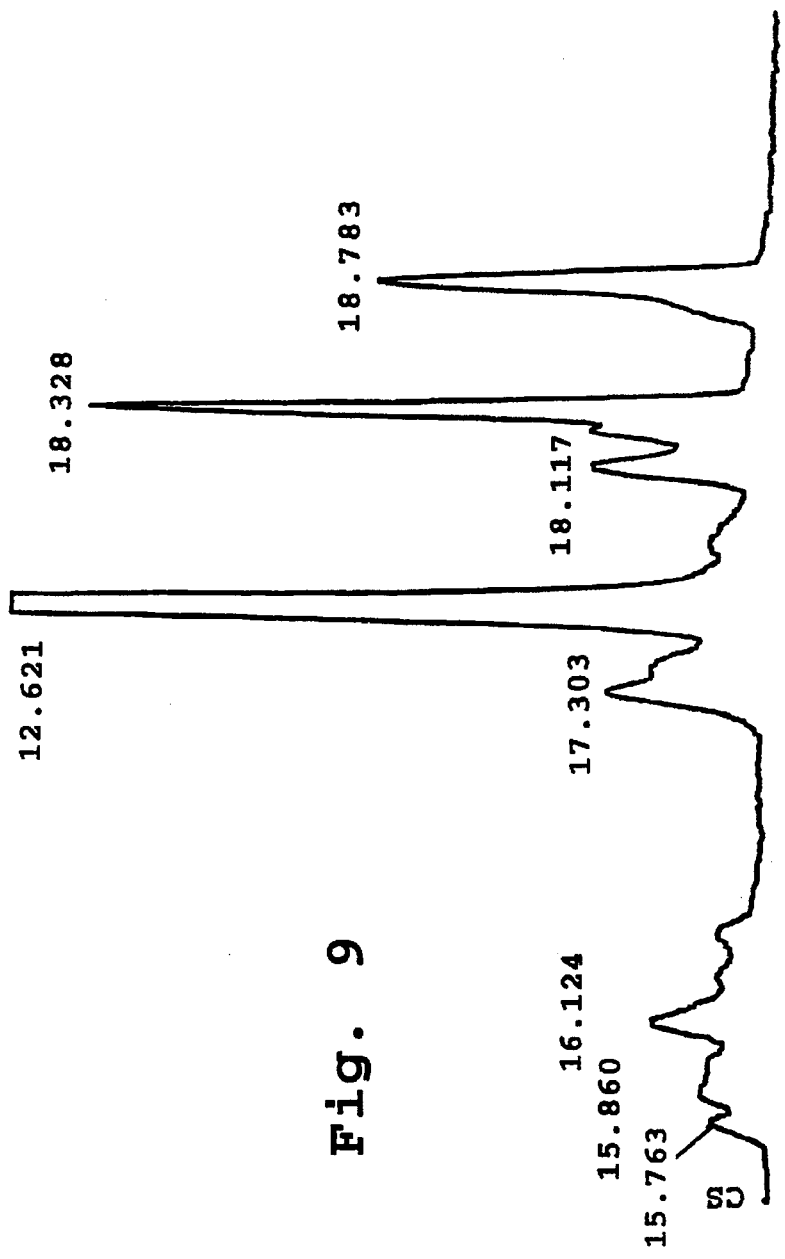
Fig. 8
Fig. 9

↓ LIGATE

↓ DENATURE, REANNEAL

↓ LIGATE

↓ DENATURE

↓ REPEAT N-2 TIMES x $2^N$

↓ POLYMERASE, LABELED dNTP

↓ Denature, reanneal

↓ RNAase H, DENATURE

↓ LIGATE, DENATURE

METHOD OF DNA SEQUENCING EMPLOYING A MIXED DNA-POLYMER CHAIN PROBE

This is a continuation of application Ser. No. 08/296,880 filed Aug. 26, 1994, which is a continuation of application Ser. No. 07/973,118, filed Nov. 6, 1992, abandoned, which is a continuation-in-part of application Ser. Nos. 07/866,018, U.S. Pat. No. 5,470,705, and 07/862,642, abandoned, filed Apr. 7, 1992 and Apr. 3, 1992, respectively.

FIELD OF THE INVENTION

The present invention relates to a probe composition, and to methods of using the composition for detecting selected sequences in a target polynucleotide.

REFERENCES

Applied Biosystems, DNA Sequencer User Bulletin, #11, "Synthesis of Fluorescent Dye-Labeled Oligonucleotides for Use as Polymers in Fluorescence-Based DNA Sequencing (1989).

Blake, et al., *Biochemistry*, 24:6132 (1985a).
Blake, et al., *Biochemistry*, 24:6139 (1985b).
Camthem et al., *J. Am Chem Soc*, 113(6324) (1991).
Cohen, A. S., et al., *Anal Chem*, 59(7):1021 (1987).
Connell, C., et al., *Biotechniques*, 5(342) (1987).
Cload, S. T., et al., *J Am Chem Soc*, 113:6324 (1991).
Froehler, et al., *Nucleic Acids Res*, 16:4831 (1988)
Hermans, J. J., *J Polymer Sd*, 18(257) (1953).
Kornberg, A., et al., "DNA Replication", pp 46–47, W. H. Freeman and Co., N.Y. (1992).
Lundegren, U., et al., *Science*, 241:1077 (1988).
Miller, P.S., et al, *Biochemistry*, 18:5134 (1979).
Miller, P.S., et al., *J Biol Chem*, 255:6959 (1980).
Miller, P.S., et al., *Bioconjugate Chem*, 1(187) (1990).
Mullis, K., et al., U.S. Pat. No. 4,683,202 (1987).
Murakami, et al., *Biochemistry*, 24:4041 (1985).
Olivera, B. M., et al., *Biopolymers*, 2(245) (1964).
Saiki, R. K., et al., *Science*, 230:1350 (1985).
Sterchak, E. P., et al., *Organic Chem*, 52:4202 (1987).
Terabe, S., et al., et al., *Anal Chem*, 57(4):834 (1985).
Towns, J. K., et al, *Anal Chem*, 63:1126 (1991).
Whiteley, N. M., et al., U.S. Pat. No. 4,883,750 (1989).
Winn-Deen, E., et al., *Clin Chem*, 37:1522 (1991).
Wu, D. Y., et al., *Genomics*, 4:560 (1989).

BACKGROUND OF THE INVENTION

A variety of DNA hybridization techniques are available for detecting the presence of one or more selected polynucleotide sequences in a sample containing a large number of sequence regions. In a simple method, which relies on fragment capture and labeling, a fragment containing a selected sequence is captured by hybridization to an immobilized probe. The captured fragment can be labeled by hybridization to a second probe which contains a detectable reporter moiety.

Another widely used method is Southern blotting. In this method, a mixture of DNA fragments in a sample are fractionated by gel electrophoresis, then fixed on a nitrocellulose filter. By reacting the filter with one or more labeled probes under hybridization conditions, the presence of bands containing the probe sequence can be identified. The method is especially useful for identifying fragments in a restriction-enzyme DNA digest which contain a given probe sequence, and for analyzing restriction-fragment length polymorphisms (RFLPs).

Another approach to detecting the presence of a given sequence or sequences in a polynucleotide sample involves selective amplification of the sequence(s) by polymerase chain reaction (Mullis, Saiko). In this method, polymers complementary to opposite end portions of the selected sequence(s) are used to promote, in conjunction with thermal cycling, successive rounds of palmer-initiated replication. The amplified sequence may be readily identified by a variety of techniques. This approach is particularly useful for detecting the presence of low-copy sequences in a polynucleotide-containing sample, e.g., for detecting pathogen sequences in a body-fluid sample.

More recently, methods of identifying known target sequences by probe ligation methods have been reported (Wu, Whiteley, Lundegren, Winn-Deen). In one approach, known as oligonucleotide ligation assay (OLA), two probes or probe elements which span a target region of interest are hybridized with the target region. Where the probe elements match (basepair with) adjacent target bases at the confronting ends of the probe elements, the two elements can be joined by ligation, e.g., by treatment with ligase. The ligated probe element is then assayed, evidencing the presence of the target sequence.

In a modification of this approach, the ligated probe elements act as a template for a pair of complementary probe elements. With continued cycles of denaturation, reannealing and ligation in the presence of the two complementary pairs of probe elements, the target sequence is amplified geometrically, allowing very small amounts of target sequence to be detected and/or amplified. This approach is also referred to as Ligase Chain Reaction (LCR).

There is a growing need, e.g., in the field of genetic screening, for methods useful in detecting the presence or absence of each of a large number of sequences in a target polynucleotide. For example, as many as 150 different mutations have been associated with cystic fibrosis. In screening for genetic predisposition to this disease, it is optimal to test all of the possible different gene sequence mutations in the subject's genomic DNA, in order to make a positive identification of a "cystic fibrosis". Ideally, one would like to test for the presence or absence of all of the possible mutation sites in a single assay.

These prior-art methods described above are not readily adaptable for use in detecting multiple selected sequences in a convenient, automated single-assay format. It is therefore desirable to provide a rapid, single-assay format for detecting the presence or absence of multiple selected sequences in a polynucleotide sample.

In another technical area, attempts to increase the throughput and degree of automation in DNA sequencing has lead to the development of sequencing approaches making use of capillary electrophoresis, e.g. Huang et al, Anal. Chem., Vol. 64, pgs. 2149–2154 (1992); Swerdiow et al, Nucleic Acids Research, Vol. 18, pgs. 1415–1419 (1990), and the like. A major impediment to the widespread application of these approaches is the requirement that gels be used in the separation medium of the capillaries. It is still very time consuming and difficult to load and/or form gels in the capillaries that have sufficiently uniform quality for reliable and convenient sequencing. High speed DNA sequencing for either diagnostic applications or for genomic analysis would make a major advance if means were available that permitted differently sized polynucleotides to be separated electrophoretically in a non-sieving liquid medium which could be readily loaded into capillaries without the time and quality control problems associated with gel separation media.

SUMMARY OF THE INVENTION

The invention is directed to a general method for altering the ratio of charge/translational frictional drag of binding polymers so that the binding polymers, which otherwise would have substantially identical ratios of charge/translational frictional drag, can be separated electrophoretically in a non-sieving liquid medium. Usually the binding polymers are polynucleotides or analogs thereof. Preferably, the charge/translational frictional drag of a binding polymer is altered by attaching to the binding polymer a polymer chain which has a different charge/translational frictional drag than that of the binding polymer. In accordance with the invention, different classes of identically-sized binding polymers can be separated by attaching different polymer chains to the binding polymers of each class so that the resulting conjugates of each class have a unique ratio of charge/translational frictional drag. Conversely, different-sized binding polymers may be separated electrophoretically in a non-sieving liquid medium by attaching substantially identical polymer chains to each size class of binding polymer so that the resultant conjugates of each class have a unique ratio of charge/translational frictional drag in the non-sieving liquid medium. The latter embodiment is particularly applicable to DNA sequencing.

The present invention includes, in one aspect, a method of detecting one or more of a plurality of different sequences in a target polynucleotide. In practicing the method, there is added to the target polynucleotide, a plurality of sequence-specific probes, each characterized by (a) a binding polymer having a probe-specific sequence of subunits designed for base-specific binding of the polymer to one of the target sequences, under selected binding conditions, and (b) attached to the binding polymer, a polymer chain having a different ratio of charge/translational frictional drag from that of the binding polymer.

The probes are reacted with the target polynucleotide under conditions favoring binding of the probes in a base-specific manner to the target polynucleotide. The probes are then treated to selectively modify those probes which are bound to the target polynucleotide in a sequence-specific manner, forming modified, labeled probes characterized by (a) a distinctive ratio of charge/translational frictional drag, and (b) a detectable reporter label.

The modified, labeled probes are fractionated by electrophoresis in a non-sieving matrix. The presence of selected sequence(s) in the target polynucleotide is detected according to the observed electrophoretic migration rates of the labeled probes.

The polymer chain may be a substantially uncharged, water-soluble chain, such as a chain composed of polyethylene oxide (PEO) units or a polypeptide chain, where the chains attached to different-sequence binding polymers have different numbers of polymer units. Electrophoresis is preferably performed under conditions of efficient heat dissipation from the nora-sieving medium, such as in a capillary tube.

In one general method, each probe includes first and second probe elements having first and second sequence-specific oligonucleotides which, when bound in a sequence specific manner to a selected single-stranded target sequence, have (or can be modified to have) confronting end subunits which can basepair to adjacent bases in the target polynucleotide sequence. After hybridizing the oligonucleotides to the target polynucleotide, the target-bound oligonucleotides are ligated, to join those hybridized oligonucleotides whose confronting end subunits are base-paired with adjacent target bases. In each pair of probe elements, one of the probe elements contains the probe-specific polymer chain, and the other element preferably includes a detectable reporter.

In a second general embodiment, each probe includes first and second primer elements having first and second sequence-specific oligonucleotide primers effective to hybridize with opposite end regions of complementary strands of a selected target polynucleotide segment. The first probe element contains the probe-specific polymer chain. The primer elements are reacted with the target polynucleotide in a series of primer-initiated polymerization cycles which are effective to amplify the target sequence of interest.

The amplification reaction may be carried out in the presence of reporter-labeled nucleosidetriphosphates, for purposes of reporter labeling the amplified sequences. Alternatively, the amplified target sequences may be labeled, in single-stranded form, by hybridization with one or more reporter-labeled, sequence-specific probes, or in double-stranded form by covalent or non-covalent attachment of a reporter, such as ethidium bromide.

In a third general embodiment, bound oligonucleotide probes are reacted with reporter-labeled nucleoside triphosphate molecules, in the presence of a DNA polymerase, to attach reporter groups to the 3' end of the probes.

In a fourth general embodiment, the probes includes a binding polymer which is modified by enzymatic cleavage when bound to a target sequence. The cleavage reaction may remove a portion of the binding polymer, to modify the probes's ratio of charge/translational frictional drag, or may separate a reporter label carried at one end of the binding polymer from a polymer chain carried at the other end of the binding polymer, to modify the charge/translational frictional drag of the binding polymer carrying the reporter label.

Also forming part of the invention is a probe composition for use in detecting one or more of a plurality of different sequences in a target polynucleotide. The composition includes a plurality of sequence-specific probes, each characterized by (a) a binding polymer having a probe-specific sequence of subunits designed for base-specific binding of the polymer to one of the target sequences, under selected binding conditions, and (b) attached to the binding polymer, a polymer chain having a ratio of charge/translational frictional drag which is different from that of the binding polymer.

In one embodiment, each sequence specific probe further includes a second binding polymer, where the first-mentioned and second binding polymers in a sequence-specific probe are effective to bind in a base-specific manner to adjacent and contiguous regions of a selected target sequence, allowing ligation of the two binding polymers when bound to the target sequence in a sequence-specific manner. The second binding polymer preferably includes a detectable label, and the polymer chain attached to the first binding polymer imparts to each ligated probe pair, a distinctive combined ratio of charge/translational frictional drag.

In another embodiment, each sequence specific probe in the composition further includes a second binding polymer, where the time-mentioned and second binding polymers in a sequence-specific probe are effective to bind in a base-specific manner to opposite end regions of opposite strands of a selected duplex target sequence, allowing primer initiated polymerization of the target region in each strand. The second binding polymer preferably includes a detectable label, and the polymer chain attached to the first binding polymer imparts to each ligated probe pair, a distinctive combined ratio of charge/translational frictional drag.

In another embodiment, each sequence-specific probe includes a binding polymer, a polymer chain attached to the binding polymer, and a reporter attached to the binding polymer.

In another important aspect, the invention includes a method and compositions for carrying out nucleic acid sequencing wherein mixtures of labelled polynucleotides each having a common origin and each terminating with a known base are separated electrophoretically by size in a non-sieving liquid medium. Preferably, identical polymer chains are combined with the labelled polynucleotides to form conjugates which are then separated by capillary electrophoresis. As described more fully below, compositions related to this embodiment include polymers with attached polymer chains. Preferably, such palmers are used in the chain-termination approach to DNA sequencing to generate a mixture of labelled polynucleotides as described above.

These and other objects and features of the invention will become more fully apparent when the following detailed description of the invention is read in conjunction with the accompanying drawings.

BRIEF DESCRIPTION OF THE DRAWINGS

FIG. 8 illustrates an idealized electrophoretic pattern observed in the FIG. 7 method, where a target polynucleotide contains mutations in two different target regions;

FIG. 9 is an electropherogram, on capillary electrophoresis, in a non-sieving medium, of labeled probes having polypeptide polymer chains, and formed by ligation of adjacent probes on a target molecule;

DETAILED DESCRIPTION OF THE INVENTION

I. Definitions

"A target polynucleotide" may include one or more nucleic acid molecules, including linear or circularized single-stranded or double-stranded RNA or DNA molecules "Target nucleic acid sequence" means a contiguous sequence of nucleotides in the target polynucleotide. A "plurality" of such sequences includes two or more nucleic acid sequences differing in base sequence at one or more nucleotide positions.

"Sequence-specific binding polymer" means a polymer effective to bind to one target nucleic acid or sequence subset sequence with base-sequence specificity, and which has a substantially lower binding affinity, under selected hybridization conditions, to any other target sequence or sequence subset in a given plurality of sequences in the test sample.

The "charge" of a polymer is the total net electrostatic charge of the polymer at a given pH;

The "translational frictional drag" of a polymer is a measure of the polymer's frictional drag as it moves electrophoretically through a defined, non-sieving liquid medium.

"Non-sieving matrix " means a liquid medium which is substantially free of a mesh or network or matrix of interconnected polymer molecules.

A "distinctive ratio of charge/translational frictional drag" of a probe is evidenced by a distinctive, i.e., unique, electrophoretic mobility of the probe in a non-sieving medium.

"Capillary electrophoresis" means electrophoresis in a capillary tube or in a capillary plate, where the diameter of separation column or thickness of the separation plate is between about 25–500 microns, allowing efficient heat dissipation throughout the separation medium, with consequently low thermal convection within the medium.

A "labeled" probe refers to a probe which is composed of a binding polymer effective to bind in a sequence-specific manner to a selected target sequence, a polymer chain which imparts to the binding polymer, a distinctive ratio of charge/translational frictional drag, and a detectable reporter or tag.

A "reporter" or "label" or "tag" refers to a fluorophore, chromophore, radioisotope, or spin label which allows direct detection of a labeled probe by a suitable detector, or a ligand, such as an antigen, or biotin, which can bind specifically and with high affinity to a detectable anti-ligand, such as a reporter-labeled antibody or avidin.

II. Probe Composition

Figure 1A:
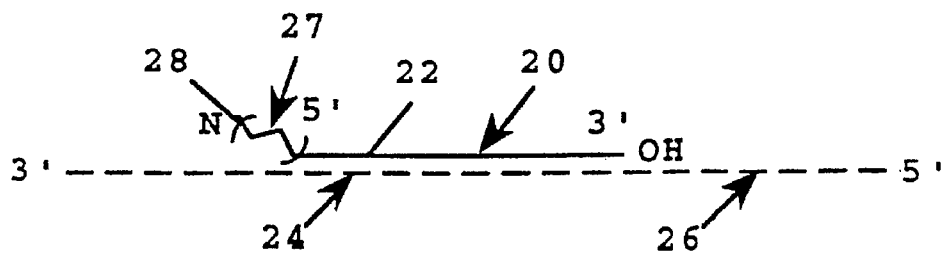
FIGS. 1A–1D illustrate three general types of probes and probe elements used in practicing various embodiments of the method of the invention.
Figure 1B:
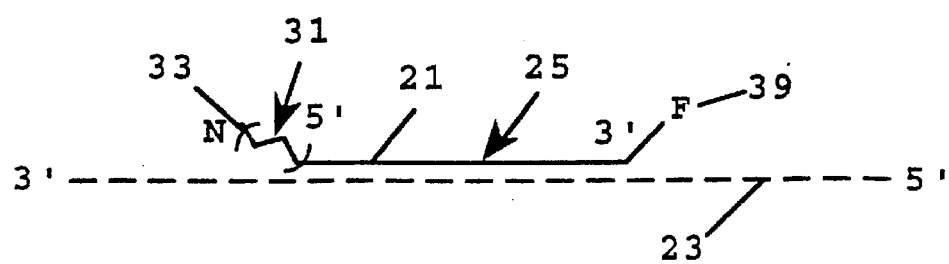
Figure 1C:
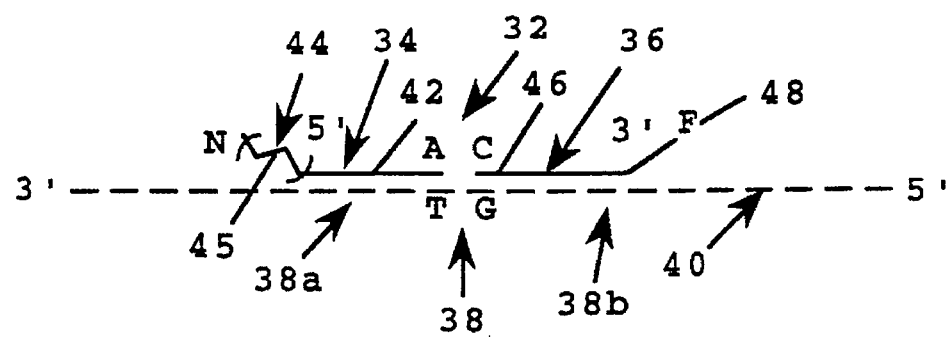

This section describes several embodiments of probes designed for use in the present invention. In the typical case, the probe is part of a probe composition which contains a plurality of probes used for detecting one or more of a plurality of target sequences, according to methods described in Section III. The probes described with reference to FIGS. 1B and 1C are representative of probes or probe elements which make-up probe compositions in accordance with the present invention.

A. Probe Structure

FIG. 1 shows a probe 20 which is one of a plurality of probes used in one embodiment of the method of the invention. As will be seen below, a probe composition containing a probe like probe 20 is designed for use in a "probe-extension" method of identifying target sequences, such as the sequence in region 24 of a target polynucleotide, indicated by dashed line at 26 in FIG. 1A.

Probe 20 includes an oligonucleotide binding polymer 22 which preferably includes at least 10–20 bases, for requisite basepair specificity, and has a base sequence which is complementary to region 24 in target polynucleotide 26, with such in single-stranded form. Other probes in the composition have sequence specificities for other target regions of known sequence in the target polynucleotide. In a preferred embodiment, the binding polymers of the different-sequence probes all have about the same length, allowing hybridization of the different probes to the target polynucleotide with substantially the same hybridization reaction kinetics and thermodynamics ($T_m$).

Other binding polymers which are analogs of polynucleotides, such as deoxynucleotides with thiophosphodiester linkages, and which are capable of base-specific binding to single-stranded or double-stranded target polynucleotides are also contemplated. Polynucleotide analogs containing uncharged, but stereoisomeric methylphosphonate linkages between the deoxydbonucleoside subunits have been reported (Miller, 1979, 1980, 1990, Murakami, Blake, 1985a, 1985b). A variety of analogous uncharged phosphoramidate-linked oligonucleotide analogs have also been reported (Froehler). Also, deoxydbonucleoside analogs having achiral and uncharged intersubunit linkages (Sterchak) and uncharged morpholino-based polymers having achiral intersubunit linkages have been reported (U.S. Pat. No. 5,034,506). Such binding polymers may be designed for sequence specific binding to a single-stranded target molecule through Watson-Crick base pairing, or sequence-specific binding to a double-stranded target polynucleotide through Hoogstein binding sites in the major groove of duplex nucleic acid (Komberg).

The binding polymer in the probe has a given ratio of charge/translational frictional drag, as defined above, and this ratio may be substantially the same for all of the different-sequence binding polymers of the plurality of probes making up the probe composition. This is evidenced by the similar migration rates of oligonucleotides having different sizes (numbers of subunits) and sequences by electrophoresis in a non sieving medium.

The oligonucleotide binding polymer in probe 20 is derivatized, at its 5' end, with a polymer chain 27 composed of N subunits 28. The units may be the subunits of the polymer or may be groups of subunits. Exemplary polymer chains are formed of polyethylene oxide, polyglycolic acid, polylactic add, polypeptide, oligosaccharide, polyurethane, polyamids, polysulfonamide, polysulfoxide, and block copolymers thereof, including polymers composed of units of multiple subunits linked by charged or uncharged linking groups.

According to an important feature of the invention, each polymer chain (or elements forming a polymer chain) imparts to the corresponding binding polymer to which it is attached, a ratio of charge/translational frictional drag which is distinctive for the associated different-sequence binding polymer. That is, the ratio of combined charge/combined translational frictional drag of the binding polymer and polymer chain, as measured at a given pH and with respect to electrophoretic polymer movement through a non-sieving liquid medium, is different for each different-sequence probe. As will be discussed below, the distinctive ratio of charge/translational frictional drag is typically achieved by differences in the lengths (number of subunits) of the polymer chain. However, differences in polymer chain charge are also contemplated, as are differences in binding-polymer length.

More generally, the polymers forming the polymer chain may be homopolymers, random copolymers, or block copolymers, and the polymer may have a linear, comb, branched, or dendritic architecture. In addition, although the invention is described herein with respect to a single polymer chain attached to an associated binding polymer at a single point, the invention also contemplates binding polymers which are derivatized by more than one polymer chain element, where the elements collectively form the polymer chain.

Preferred polymer chains are those which are hydrophilic, or at least sufficiently hydrophilic when bound to the oligonucleotide binding polymer to ensure that the probe is readily soluble in aqueous medium. The polymer chain should also not effect the hybridization reaction. Where the binding polymers are highly charged, as in the case of oligonucleotides, the polymer chains are preferably uncharged or have a charge/subunit density which is substantially less than that of the binding polymer.

Methods of synthesizing selected-length polymer chains, either separately or as part of a single-probe solid-phase synthetic method, are described below, along with preferred properties of the polymer chains.

Figure 2:
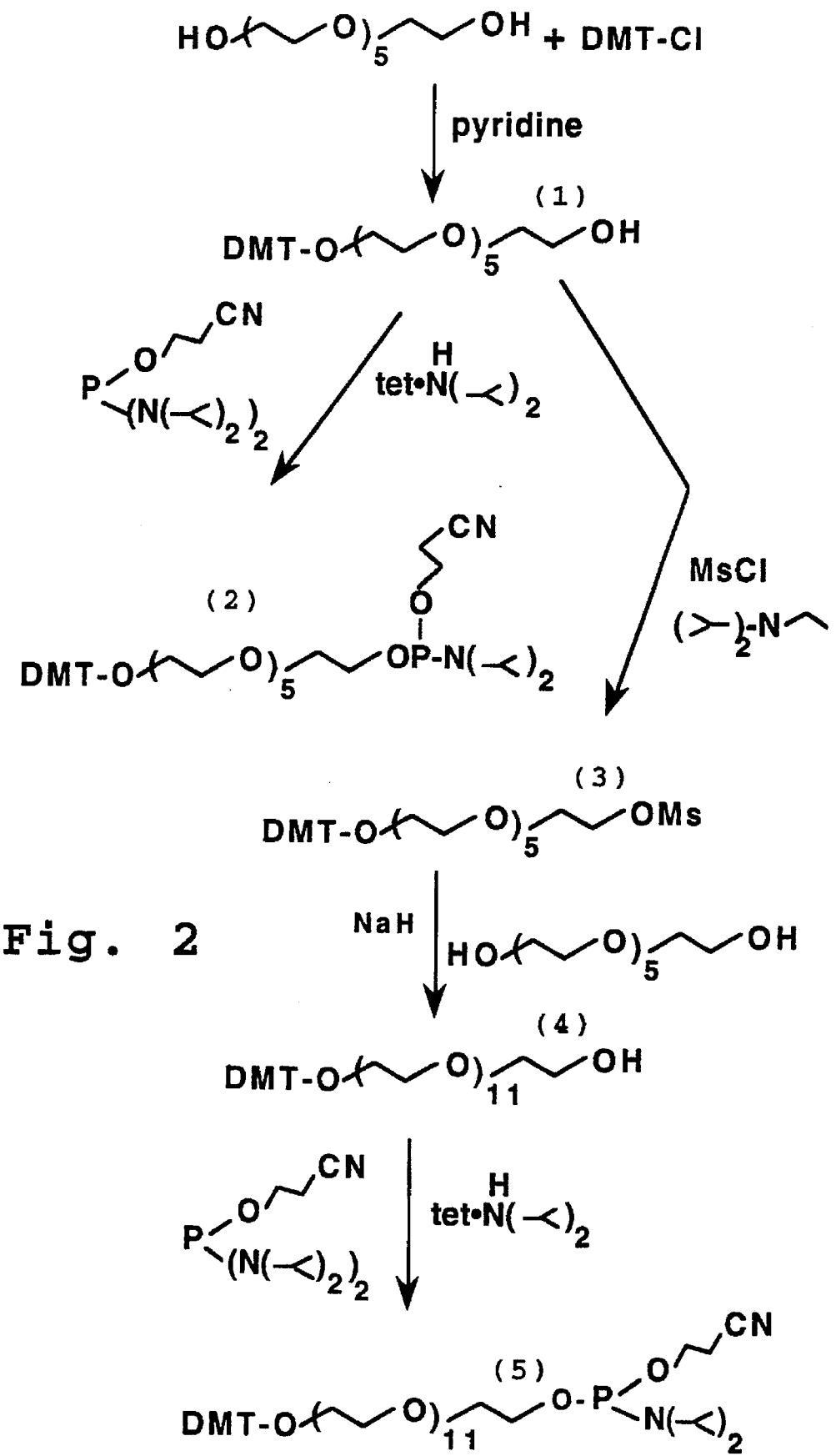
FIG. 2 illustrates methods of synthesis of polyethylene oxide polymer chains having a selected number of hexapolyethylene oxide (HEO) units.

In one preferred embodiment, described below, the polymer chain is formed of hexaethylene oxide (HEO) units, where the HEO units are joined end-to-end to form an unbroken chain of ethylene oxide subunits, as illustrated in FIG. 2, or are joined by charged (FIGS. 3A and 3B) or uncharged (FIG. 5) linkages, as described below. Other embodiments exemplified below include a chain composed of N 12 mer PEO units, and a chain composed of N tetrapeptide units.

B. Probe Compositions

This section describes three additional probes or probe-element pairs which are useful in specific embodiments of the method of the invention and which themselves, either as single probes or as probe sets, form compositions in accordance with the invention.

FIG. 1B illustrates a probe 25 which has a sequence-specific oligonucleotide binding polymer 21 designed for sequence-specific binding to a region of a single-stranded target polynucleotide 23. As will be seen with reference to FIG. 17 below, the binding polymer may contain both DNA and RNA segments. Attached to the binding polymer, at its 5' end, is a polymer chain 31 composed of N units 33, which imparts to the binding polymer a distinctive ratio of charge/translational frictional drag, as described above. The 3' end of the binding polymer is derivatized with a reporter or tag 39. In one aspect, the invention includes a composition which includes a plurality of such probes, each with a different sequence binding polymer targeted against different target regions of interest, and each with a distinctive ratio of charge/translational frictional drag imparted by the associated polymer chain.

FIG. 1C illustrates a probe 32 which consists of first and second probe elements 34, 36, is designed particularly for detecting selected sequences in each of one or more regions, such as region 38, of a target polynucleotide, indicated by dashed line 40.

In the embodiment illustrated, the sequences of interest may involve mutations, for example, point mutations, or addition or deletion type mutations involving one or a small number of bases. In a typical example, the expected site of mutation is near the midpoint of the known-sequence target region, and divides that region into two subregions. In the example shown, the mutation is a point mutation, and the expected site of the mutation is at one of the two adjacent bases T-G, with the T base defining the 5' end of a subregion 38a, and the adjacent G base, defining the 3' end of adjacent subregion 38b. As will be seen below, the probe elements are also useful for detecting a variety of other types of target sequences, e.g., sequences related to pathogens or specific genomic gene sequences.

Probe element 32, which is representative of the first probe elements in the probe composition, is composed of an oligonucleotide binding polymer element 42 which to preferably includes at least 10–20 bases, for requisite basepair specificity, and has a base sequence which is complementary to a subregion 38a in the target polynucleotide. In particular, the 3' end nucleotide bases are selected for base pairing to the 5' end nucleotide bases of the corresponding subregion, e.g., the A:T matching indicated. The oligonucleotide in the first probe element is derivatized, at its 5' end, with a polymer chain 44 composed of N preferably repeating units 45, substantially as described with respect to chain 27 formed from units 28. As described with respect to probe 20, the polymer chain in the first probe element imparts a ratio of charge/translational frictional drag which is distinctive for each sequence-specific probe element in the composition.

Second probe element 36, which is also representative of the second probe elements in the probe composition, is composed of an oligonucleotide polymer binding element 46 which preferably includes at least 10–20 bases, for requisite basepair specificity, and has a base sequence which is complementary to a subregion 38b in the target polynucleotide. In particular, the 5' end nucleotide bases are selected for base pairing to the 3' end nucleotide bases of the corresponding subregion, e.g., the C:G matching indicated.

As seen in FIG. 1B, when the two probe elements are both hybridized to their associated target regions, the confronting end subunits in the two probes, in this example the confronting A and C bases, are matched with adjacent bases, e.g., the adjacent T and G bases in the target polynucleotide. In this condition, the two probe elements may be ligated at their confronting ends, in accordance with one embodiment of the invention described below, forming a ligated probe which contains beth oligonucleotide elements, and has the sequence-specific polymer chain and a reporter attached at opposite ends of the joined olignucleotides. It will be recognized that the condition of abutting bases in the two probes can also be produced, after hybridization of the probes to a target region, by removing overlapping deoxy-dbenucleotides by exonuctease treatment.

The second probe element is preferably labeled, for example, at its 3' end, with detectable reporter, such as reporter F indicated at 48 in FIG. 1B. Preferably the reporter is an optical reporter, such as a fluorescent molecule which can be readily detected by an optical detection system. A number of standard fluorescent labels, such as FAM, JOE, TAMRA, and ROX, which can be detected at different excitation wavelengths, and methods of reporter attachment to oligonucteotides, have been reported (Applied Biosystems, Connell).

In one embodiment, each probe includes two second probe elements, one element having an end-subunit base sequence which can basepair with a wildtype bases in the target sequence, and a second element having an end-subunit base sequence which can basepair with an expected mutation in the sequence. The two alternative elements are labeled with distinguishable reporters, allowing for positive identification of wildtype or mutation sequences in each target region, as will be described in Section III below. Alternatively, the two second probe elements (e.g., oligonucleotides) may have the same reporters, and the first probe elements have polymer chains which impart to the two probe elements, different ratios of charge/translational frictional drag, allowing the two target regions to be distinguished on the basis of electrophoretic mobility.

Figure 1D:
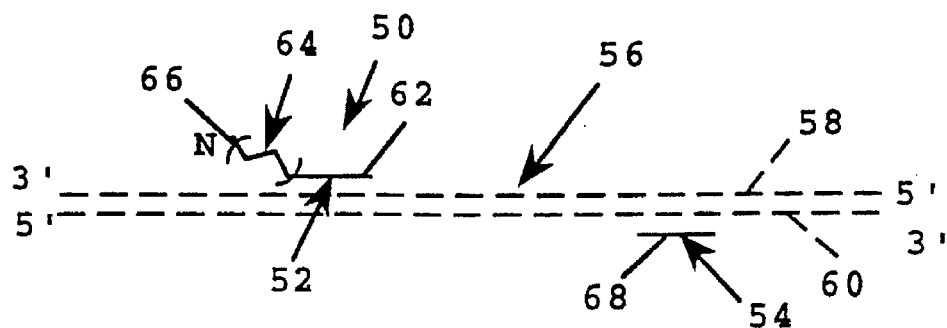

FIG. 1D shows a probe 50 which is representative of probes in a composition designed for use in another embodiment of the method of the invention. The probe, which consists of first and second palmer elements 52, 54, is designed particularly for detecting the presence or absence of regions in a double-stranded target polynucleotide which are bounded by the palmer-element sequences. In the example shown in FIG. 1D, the region bounded by the palmer sequence is indicated at 56, and the two strands of a double-stranded target polynucleotide, by the dashed lines 58, 60.

Polymer element 52, which is representative of the first primer elements in the probe composition, is composed of an oligonucleotide palmer element 62 which preferably includes at least 7–15 bases, for requisite basepair specificity, and has a base sequence which is complementary to a 3'-end portion of region 56 in one of the two target strands, in this case, strand 58.

The oligonucleotide polymer is derivatized, at its 5' end, with a polymer chain 64 composed of N preferably repeating units 66, substantially as described with respect to chain 27 formed from units 28. As described with respect to probe 20, the polymer chain in the first probe element imparts a ratio of charge/translational frictional drag which is distinctive for each sequence-specific polymer element in the composition.

Second palmer element 54, which is also representative of the second probe elements in the probe composition, is composed of an oligonucleotide palmer element 68 which also preferably includes at least 7–15 bases, for requisite basepair specificity, and has a base sequence which is complementary to a 5' end portion of the opposite strand—in this case, strand 60, of the duplex DNA forming region 56.

The second primer element may be labeled with a detectable reporter, as described above. Alternatively, labeling can occur after formation of amplified target sequences, as described below.

C. Probe Preparation

Methods of preparing polymer chains in the probes generally follow known polymer subunit synthesis methods. Methods of forming selected-length PEO chains are discussed below, and detailed in Examples 1–4. These methods, which involve coupling of defined-size, multi-subunit polymer units to one another, either directly or through charged or unchanged linking groups, are generally applicable to a wide variety of polymers, such as polyethylene oxide, polyglycolic acid, polylactic acid, polyurethane polymers, and oligosaccharides.

The methods of polymer unit coupling are suitable for synthesizing selected-length copolymers, e.g., copolymers of polyethylene oxide units alternating with polypropylene units. Polypeptides of selected lengths and amino acid composition, either homopolymer or mixed polymer, can be synthesized by standard solid-phase methods, as outlined in Example 5.

FIG. 2 illustrates one method for preparing PEO chains having a selected number of HEO units. As shown in the figure, HEO is protected at one end with dimethoxytrityl (DMT), and activated at its other end with methane sulfonate. The activated HEO can then react with a second DMT-protected HEO group to form a DMT-protected HEO dimer. This unit-addition is carried out successively until a desired PEO chain length is achieved. Details of the method are given in Example 1.

Example 2 describes the sequential coupling of HEO units through uncharged bisurethane tolyl groups. Briefly, with respect to FIG. 3, HEO is reacted with 2 units of tolyene-2,4-diisocyanate under mild conditions, and the activated HEO is then coupled at both ends with HEO to form a bisurethane tolyl-linked tdmer of HEO.

Figure 4A:
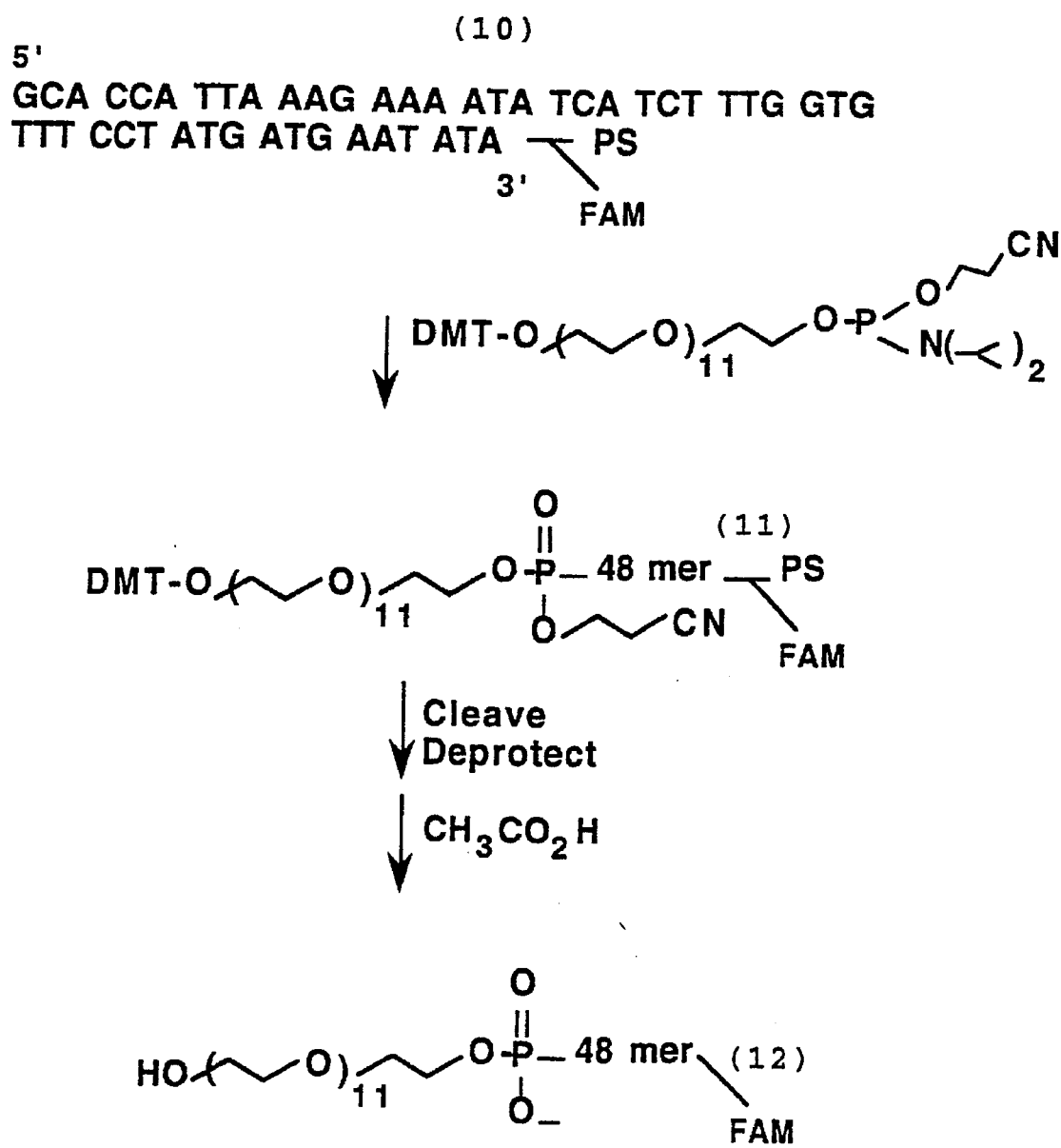
FIGS. 4A and 4B illustrate coupling reactions for coupling the polymer chains of FIGS. 2 and 3A and 3B to the 5' end of a polynucleotide, respectively.
Figure 4B:
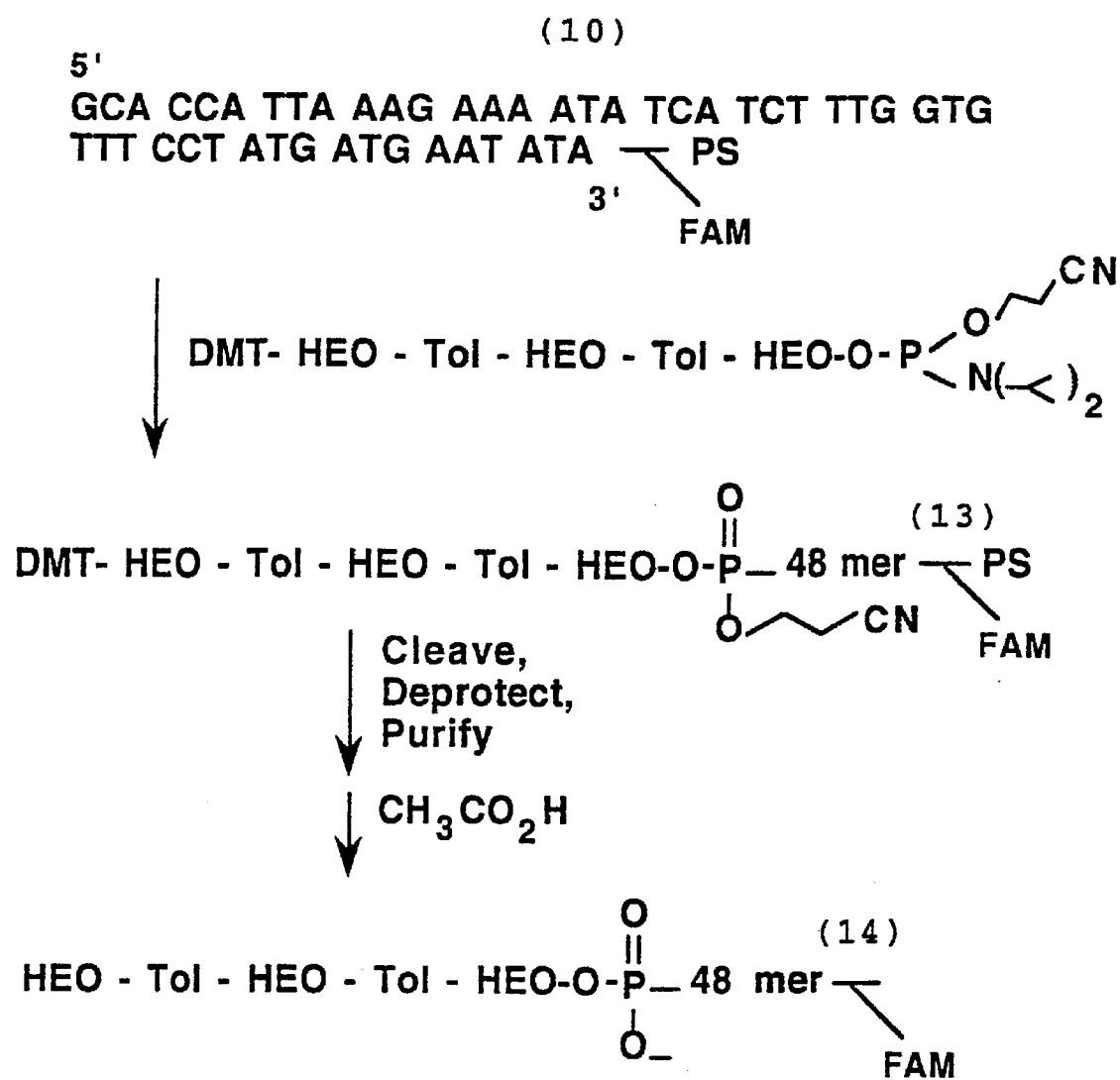

Coupling of the polymer chains to an oligonucleotide can be carried out by an extension of conventional phosphoramidite oligonucleotide synthesis methods, or by other standard coupling methods. FIG. 4A illustrates the coupling of a PEO polymer chain to the 5' end of an oligonucleotide formed on a solid support, via phosphoramidite coupling. FIG. 4B illustrates the coupling of the above bisurethane tolyl-linked polymer chain to an oligonucleotide on a solid support, also via phosphoramidite coupling. Details of the two coupling methods are given in Examples 3B and 3C, respectively.

Figure 5:
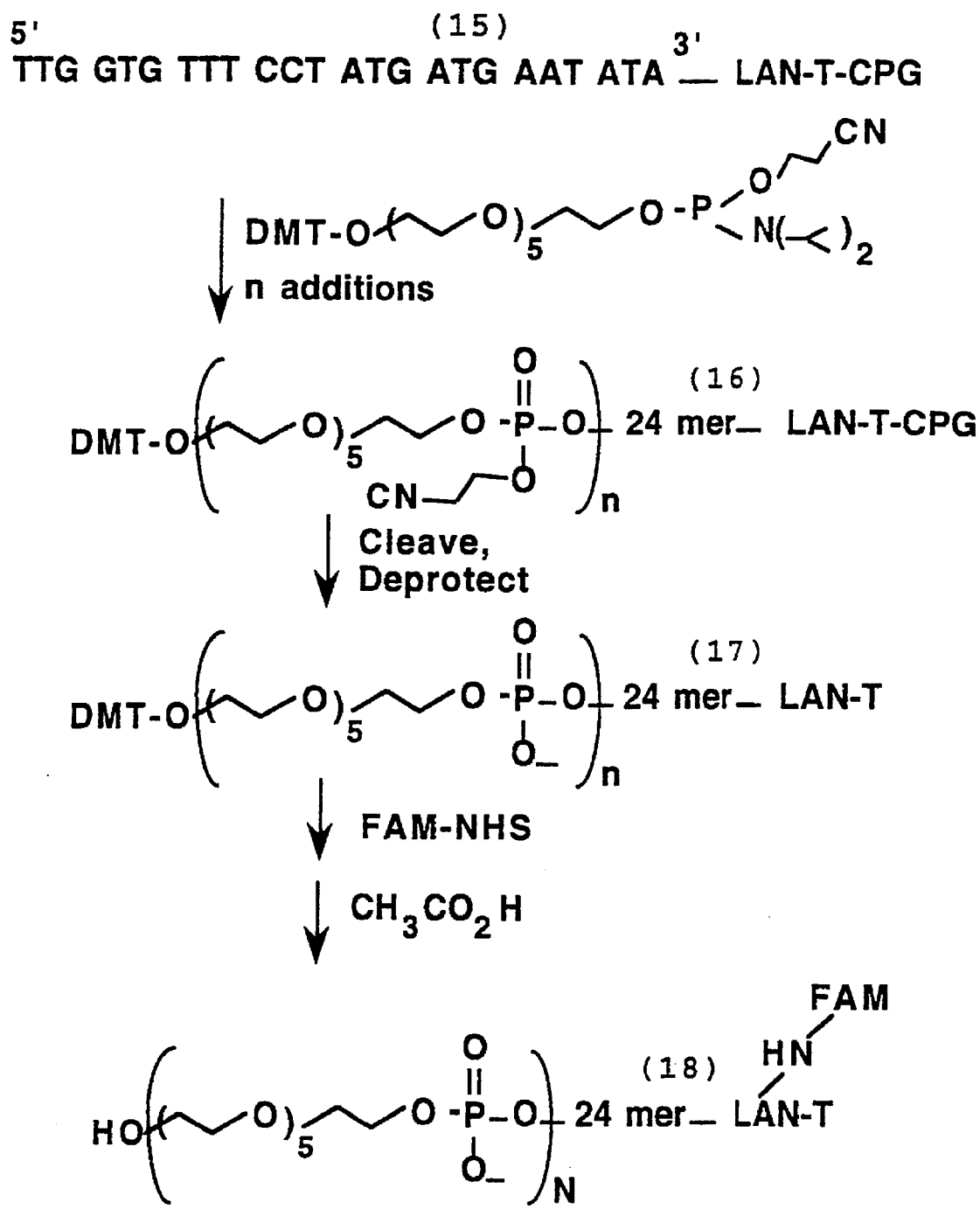
FIG. 5 shows the reaction steps for adding HEO units successively to an oligonucleotide through phosphodiester linkages, and subsequent fluorescent tagging.

Alternatively, the polymer chain can be built up on an oligonucleotide (or other sequence-specific binding polymer) by stepwise addition of polymer-chain units to the oligonucleotide, using standard solid-phase synthesis methods. FIG. 5 illustrates the stepwise addition of HEO units to an oligonucleotide formed by solid-phase synthesis on a solid support. Essentially, the method follows the same phosphoramidite activation and deprotection steps used in building up the stepwise nucleotide addition. Details are given in Example 4. Example 5 describes a similar method for forming a selected-length polypeptide chain on an oligonucleotide.

As noted above, the polymer chain imparts to its probe, a ratio of charge/translational frictional drag which is distinctive for each different-sequence probe. The contribution which the polymer chain makes to the derivatized binding polymer will in general depend on the subunit length of the polymer chain. However, addition of charge groups to the polymer chain, such as charged linking groups in the PEO chain illustrated in FIG. 5, or charged amino acids in a polypeptide chain, can also be used to achieve selected charge/frictional drag characteristics in the probe.

III. Electrophoretic Separation of Labeled Probes in Non-Sieving Medium

According to an important feature of the invention, probes having different-length and/or different-sequence binding polymers, which themselves cannot be resolved by electrophoresis in a non-sieving medium, can be finely resolved by derivatization with polymer chains having slightly different size and/or charge differences.

In one preferred approach, the probes are fractionated by capillary electrophoresis in a non-sieving matrix, as defined above. The advantage of capillary electrophoresis is that efficient heat dissipation reduces or substantially eliminates thermal connections within the medium, thus improving the resolution obtainable by electrophoresis.

Electrophoresis, such as capillary electrophoresis, (CE) is carried out by standard methods, and using conventional CE equipment, except that the electrophoresis medium itself does not contain a sieving matrix. The CE protocol described in Example 6 is exemplary.

Figure 6:
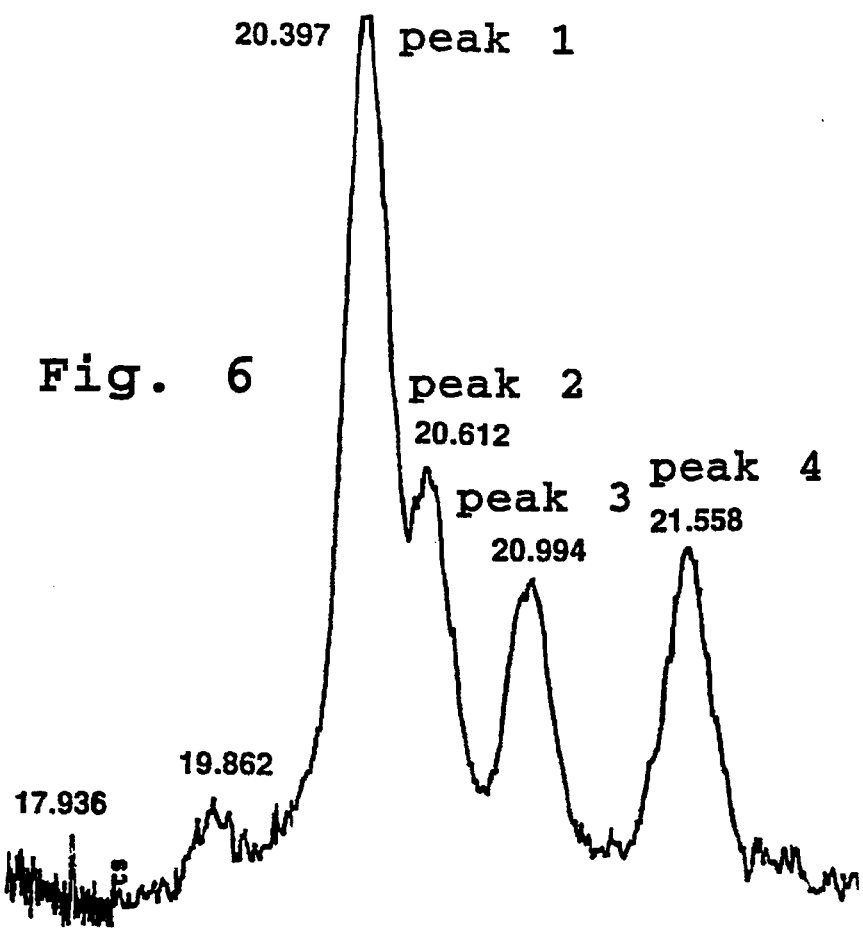
FIG. 6 is an electropherogram, on capillary electrophoresis in a non-sieving medium, of a 24 base oligonucleotide before (peak 1) and after derivatization with 1 (peak 2), 2 (peak 3), and 4 (peak 4) units of a hexaethylene oxide (HEO) unit.

FIG. 6 shows an electropherogram of fluorescent-labeled 24-base oligonucleotide probes which are either underivatized (peak 1), or derivatized at their 5' ends with a 1,2, or 4 phosphate-linked HEO subunits (peaks 2, 3, and 4, respectively). The probes were prepared as described in Example 4, and capillary electrophoresis was carried out in a buffer medium under the conditions detailed in Example 6.

As seen in the figure, the probes are well resolved into four peaks, with migration times of 20.397, 20.612, 20.994, and 21.558 minutes. In the absence of the polymer chains, the four oligonucleotide probes would migrate at the same or substantially the same electrophoretic migration rate, i.e., would tend to run in a single unresolved peak. (This would be true whether or not the oligonucleotides had the same or different sizes (Olivera, Hermans)).

The ability to fractionate charged binding polymers, such as oligonucleotides, by electrophoresis in the absence of a sieving matrix offers a number of advantages. One of these is the ability to fractionate charged polymers all having about the same size. As will be appreciated in Section IV below, this feature allows the probes in the probe composition to have similar sizes, and thus similar hybridization kinetics and thermodynamics ($T_m$) with the target polynucleotide. Another advantage is the greater convenience of electrophoresis, particularly CE, where sieving polymers and particularly problems of forming and removing crosslinked gels in a capillary tube are avoided.

IV. Assay Method

In one aspect, the method of the invention is designed for detecting one or more different-sequence regions in a target polynucleotide. The method includes first adding to the target polynucleotide, a plurality of sequence-specific probes of the type described above. The probes are reacted with the target polynucleotide under conditions which favor sequence-specific binding of the probes to corresponding sequences in the target polynucleotide. As indicated above, this binding typically involves hybridization of complementary base sequences in the target and probe by Watson-Crick base pairing.

Alternatively, base-specific hydrogen-bond paidng between a single-strand probe and double-stranded target sequences, via Hoogstein base pairing, typically in the major groove of the duplex molecule (Komberg), is also contemplated.

Following probe binding to the target polynucleotide, the probes are treated to selectively label probes bound to the target sequences in a sequence-specific manner. This may involve joining probe elements by ligation, such as enzymatic ligation, across an expected mutation site, primer-initiated amplification of selected target sequences, probe extension in the presence of labeled nucleoside triphosphate molecules, or enzymatic cleavage of a probe bound to a target region, as described below.

The labeled probes produced by selective modification of target-bound probes are fractionated by electrophoresis in a non-sieving medium, as discussed in Section III above. The migration rates of the modified, labeled probes can be used to identify the particular sequence associated with the labeled probes, to identify the presence of particular sequences in the target polynucleotide.

A. Probe-Ligation Method

This embodiment is designed especially for detecting specific sequences in one or more regions of a target polynucleotide. The target polynucleotide may be a single molecule of double-stranded or single-stranded polynucleotide, such as a length of genomic DNA, cDNA or vital genome including RNA, or a mixture of polynucleotide fragments, such as genomic DNA fragments or a mixture of viral and somatic polynucleotide fragments from an infected sample. Typically, in the present embodiment, the target polynucleotide is double-stranded DNA which is denatured, e.g., by heating, to form single-stranded target molecules capable of hybridizing with probe binding polymers.

Figure 7A:
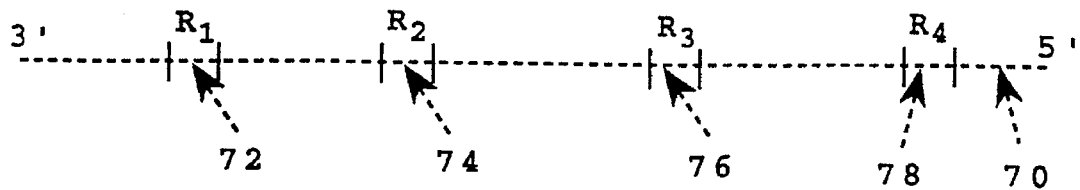
FIGS. 7A–7D illustrate an embodiment of the invention in which a target sequence is detected by ligation (OLA) of base-matched probe elements.

FIG. 7A shows a portion of a single-stranded target polynucleotide 70, e.g., the "+" strand of a double-stranded target, with the 3' to 5' orientation shown. The polynucleotide contains a plurality of regions $R_1$, $R_2$, $R_3$ to $R_n$, indicated at 72, 74, 76, and 78, respectively, which each contain a different base sequence. Each region preferably has about the same length, i.e., number of basepairs, preferably between about 20–80 basepairs. The total number of regions $R_n$ which are to be assayed in the method may be up to hundred or more, although the method is also applicable where only a few different sequence regions are to be detected.

Although the method is illustrated in FIG. 7 with respect to a point mutation, it will be appreciated how other types of small mutational events, such as deletion or addition of one or more bases, can be detected by the method. More generally, the method can be used to assay, simultaneously, target sequences, such as sequences associated with a mixture of pathogen specimens, or gone sequences in a genomic DNA fragment mixture.

Figure 7B:
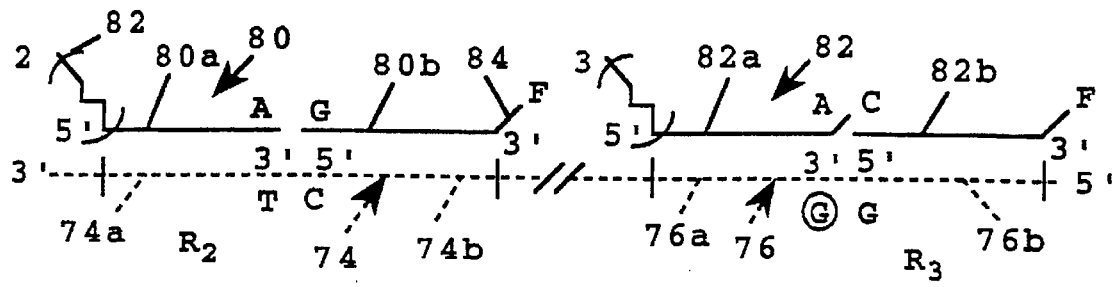
Figure 7C:
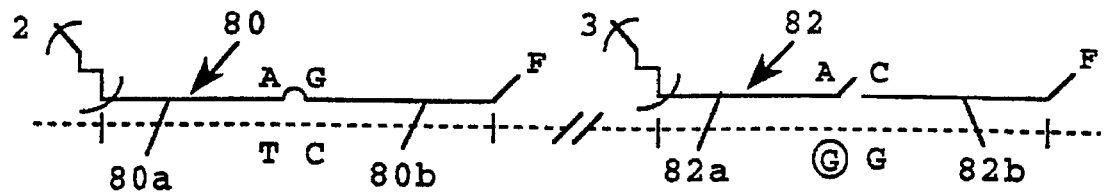

FIG. 7B shows an enlarged portion of target polynucleotide 70 which includes regions 74 ($R_2$) and 76 ($R_3$). Region 74 includes adjacent bases T and C, as shown which divide the region into two subregions 74a, 74b terminating at these two bases. The T and C bases are wildtype (non-mutated) bases, but one of these bases, e.g., the T base, corresponds to a known point-mutation site of interest. Similarly, region 76 includes adjacent bases G and G which divide this region into two subregions 76a, 76b terminating at these two bases. The G base in subregion 76a represents a point mutation from a wildtype T base, and the adjacent G base is non-mutated. The assay method is designed to identify regions of the target, such as regions 74 and/or 76, which contain such point mutations.

The probe composition used in the assay method is composed of a plurality of probe elements, such as those described with respect to FIG. 1B above. This composition is added to the target polynucleotide, with such in a denatured form, and the components are annealed to hybridize the probe elements to the complementary-sequence target regions, as shown in FIG. 1B.

One of the probes in the composition, indicated at 80, includes a pair of probe elements 80a, 80b whose sequence are complementary to the corresponding subregions 74a, 74b, respectively in region 74 of the target polynucleotide i.e., the probe element sequences correspond to those of the "_" strand of the $R_2$ region of the target. In particular, the probe elements have end-subunits A and G bases which, when the elements are hybridized to complementary subregions of region 74, as shown, are effective to form Watson-Crick base paidng with adjacent bases T and C in the target region.

Another of the probes in the composition, indicated at 82, includes a pair of probe elements 82a, 82b whose sequence are complementary to the corresponding subregions 76a, 76b, respectively in region 76 of the target polynucleotide. In this case, the probe elements have end-subunits A and C bases which, when the elements are hybridized to complementary subregions of region 76, as shown, are effective to form Watson-Crick base pairing with adjacent bases T and G bases in the wildtype target region. However, in the example shown, a T to G mutation prevents Watson-Crick base paidng of the A endsubunit to the associated target base.

Following annealing of the probe elements to corresponding target sequences, the reaction mixture is treated with ligating reagent, preferably a ligase enzyme, to ligate pairs of probe elements whose confronting bases are base-paired with adjacent target bases. Typical ligation reaction conditions are given in Example 7A. The ligation reaction is selective for those probe elements whose end subunits are base-paired with the target bases. Thus, in the example illustrated, the probe elements 80a, 80b are ligated, but probe elements 82a, 82b are not.

Figure 7D:
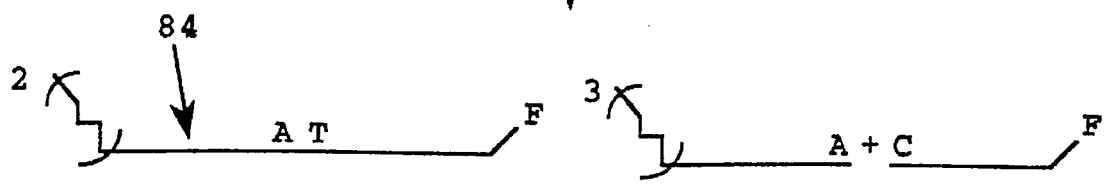

It can be appreciated that the ligation reaction joins an oligonucleotide carrying a sequence-specific polymer chain to an oligonucleotide carrying a detectable reporter, selectively forming labeled, ligated probes, such as ligated probe 84, composed of an oligonucleotide labeled at one end with a probe-specific polymer chain and at its other end with a detectable (fluorescent) reporter. Denaturing the target-probe complexes, as illustrated in FIG. 7D, releases a mixture of ligated, labeled probes, corresponding to wildtype target sequences, and non-ligated probe elements corresponding to point mutations at or near probe element end subunits. Each ligated, labeled probe has a polymer chain which imparts to that probe, a distinctive ratio of charge/translational frictional drag, as discussed above.

In the assay method illustrated in FIGS. 7A–7D, one of the target regions ($R_3$) contained a mutation which prevents ligation of the complementary-sequence probe elements. It is assumed, by way of example, that the entire target polynucleotide contains eight sequence regions of interest, of which regions $R_3$ and $R_7$ have mutations of the type which prevent probe-element ligation, and the other six regions are wildtype sequences which lead to ligated, labeled probes. FIG. 8 shows an idealized electrophoretic pattern which would be expected in the ligation assay method. Peaks 1–8 in the figure are the expected migration times of ligated oligonucleotide probes having increasingly longer polymer chains, such as 1, 2, 3, 4, 5, 5, 7, and 8 linked HEO units. The observed electrophoretic pattern will show gaps at the 3 and 7 peak positions, as indicated, evidencing mutations in the 3 and 7 target positions. All unmodified DNA will elute substantially with the N=0 peak.

Example 7 illustrates the general principles of probe ligation and separation, in accordance with this aspect of the invention. In this method, a 25-base oligonucleotide derivatized with 1 or 2 Phe-Ala-Phe-Al a tetrapeptide units and a fluorescent-labeled 25-base oligonucleotide were mixed under hybridization conditions with a target polynucleotide whose sequence spanned the two oligonucleotides. The hybridized probe elements were treated with ligase, to form fluorescent-labeled probes with carrying 1 or 2 tetrapeptide units.

Capillary electrophoresis in a non-sieving, denaturing medium was carried out substantially as described above, and as detailed in Example 7. FIG. 9 shows the electropherogram of the fluorescent-labeled probe before ligation (peak 12.621), and the same probe when ligated with a probe containing 4-, or 8-amino add polymer chains. As seen, the two ligated probes (peaks 18.328 and 18.783) and the unligated probe (peak 12.621) are easily resolved by CE in a non-sieving medium.

In the above OLA ligation method, the concentration of probe can be enhanced, if necessary, by amplification of the derivatized probes with repeated probe element hybridization and ligation steps. Simple additive amplification can be achieved using the target polynucleotide as a target and repeating the denaturation, annealing, and probe element ligation steps until a desired concentration of derivatized probe is reached.

Figure 10A:
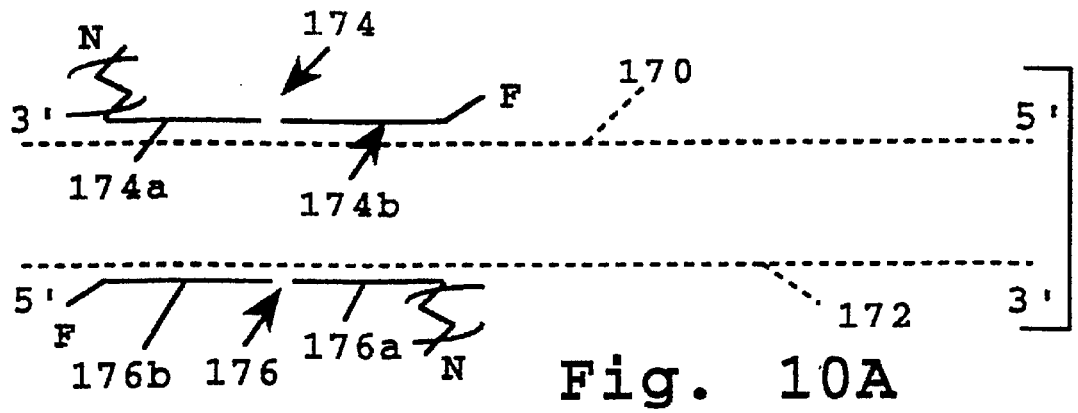
FIGS. 10A–10C illustrate an embodiment of the invention in which a mutation is detected by ligation of base-matched probes by ligase chain reaction (LCR) in accordance with the present invention.

Alternatively, the ligated probes formed by target hybridization and ligation can be amplified by ligase chain reaction (LCR), according to published methods (Winn-Deen), and also as described in Example 8. In this method, illustrated in FIGS. 10A–10C, two sets of sequence-specific probes, such as described with respect to FIG. 1B, are employed for each target region of a double-stranded DNA, whose two strands are indicated at 170 and 172 in FIG. 10A. One probe set, indicated at 174, includes probe elements 174a, 174b which are designed for sequence specific binding at adjacent, contiguous regions of a target sequence on strand 170, as indicated, and a second probe set indicated at 176, includes probe elements 176a, 176b which are designed sequence specific binding at adjacent, contiguous regions of a target sequence on opposite strand 172, also as shown.

Figure 10B:
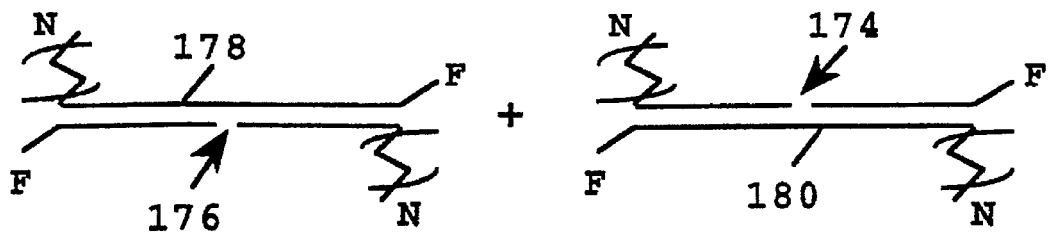
Figure 10C:
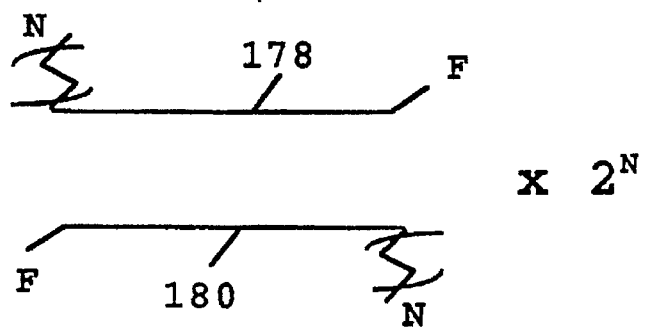

As seen, probe elements 174a and 176a are derivatized with a polymer chain, and probe elements 174b, 176b, with a fluorescent reporter, analogous to probe set 32 described above with respect to FIG. 1B. After hybridization of the two probe sets to the denatured single-stranded target sequences, the probe elements bound to each target region are ligated, and the reaction products are denatured to release labeled probes 178, 180 (FIG. 10B). These labeled probes can now serve as target substrates for binding of probe sets 174, 176, as shown in FIG. 10B, with ligation now producing 22 labeled probes. This process is repeated, i.e., N-2 times, to produce ideally a total of 2N labeled probes 178, 180, as indicated in FIG. 10C.

In the method described in Example 8 two pairs of probe elements were prepared, one set containing a first probe which is derivatized with a polymer chain containing either 2 or 4 dodeca ethylene oxide (DOE) units, as above, and a second probe which is labeled with a fluorescence reporter (JOE). The pairs of probe elements were targeted against the F508 region of the cystic fibrosis gone.

Figure 11:
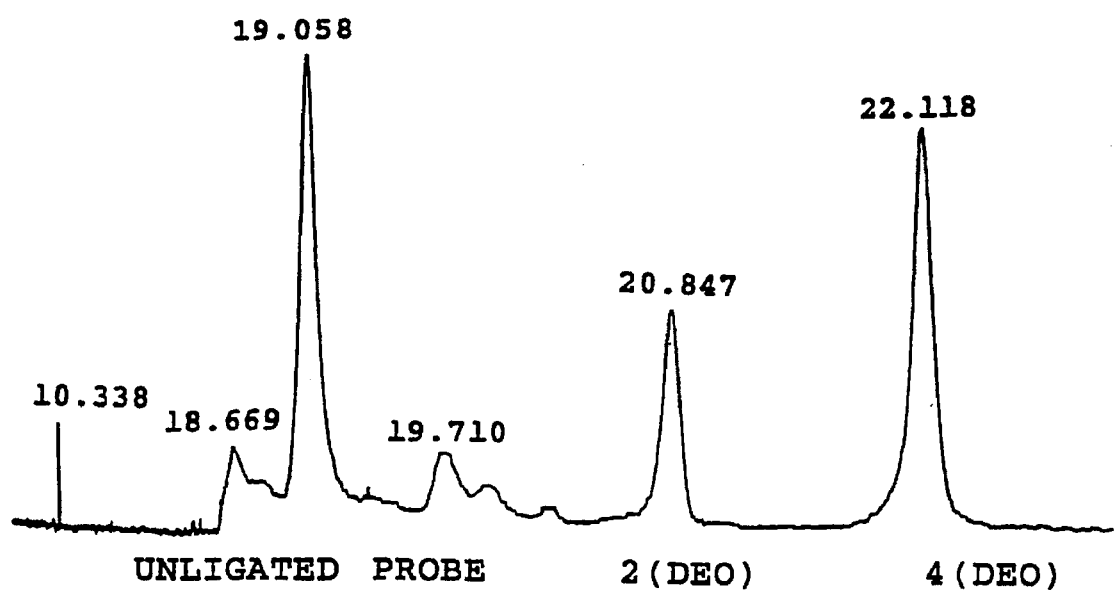
FIG. 11 is an electropherogram, on capillary electrophoresis in a non-sieving matrix, of labeled probes having polyethylene oxide polymer chains, and formed by LCR reaction.

After 30 LCR cycles, DNA from the two reaction mixtures was combined and the amplified, ligated probes in the mixture were fractionated by CE in a non-sieving buffer under denaturing conditions (8M urea). The electropherogram is shown in FIG. 11. Here the peak at the left (peak 19.058) is the unligated JOE-labeled probe. The peaks at 20.847 and 22.118 are the ligated, amplified probes containing either two or four DEO unit chains, respectively. As seen, the two probes having different length polymer chains are well resolved from one another and from probes lacking a polymer chain in a non-sieving matrix.

Although the probe-ligation method has been described above with respect to detecting mutations in each of a plurality of target regions, it is understood that the method is also applicable to detecting multiple target sequences related, for example, to the presence or absence of different pathogen sequences, or different genomic sequences in a higher organism.

Figure 18A:
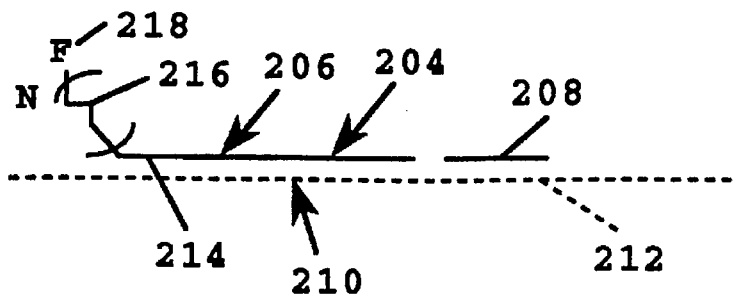
FIGS. 18A and 18B illustrate an alternative method for forming modified, labeled probes, in accordance with another embodiment of the invention.
Figure 18B:
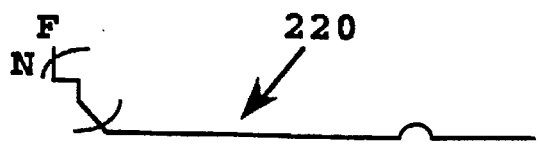

A modification of this general method is illustrated in FIGS. 18A and 18B. In this method, each sequence specific probe, such as probe 204, includes a pair of probe elements, such as elements 206,208, which are designed for binding to adjacent portions of selected sequence, such as sequence 210 in a target polynucleotide 212. Probe 206 includes a binding polymer 214, a polymer chain 216 which imparts a distinctive charge/translational frictional drag to the probe element, and a reporter 218 which may be attached to the polymer chain or binding polymer. The second probe element is an oligonucleotide which is ligatable with probe element 206, when the two elements are hybridized to the associated target sequence, as described above with respect to FIGS. 7A–7D.

The probes are hybridized to the target polynucleotide, ligated, and released, as described above, to yield a modified labeled probe 220 whose charge/translational frictional drag ratio has been modified by virtue of the different ratio of polynucleotide/polymer chain contributions to the probe after ligation. The modified probes are then fractionated by electrophoresis in a non-sieving medium, as above, to identify probes associated with different target sequences of interest.

It will be appreciated that ligation of two oligonucleotides, in the absence of polymer chain, will not alter the electrophoretic mobility of the probe in a non-sieving matrix, since the charge/translational frictional drag of the probe remains substantially unaffected by polymer length. In the present case, however, the different contributions of the polymer chain and binding polymer to the combined charge and translational frictional drag of the probe makes this ratio sensitive to the length of the binding polymer.**

B. Target-Sequence Amplification

In a second general embodiment of the method, illustrated in FIG. 12, the probes are designed for palmer-initiated amplification of one or more regions of the double-stranded target polynucleotide. At least one strand of the amplified target regions carries a polymer chain which imparts to each amplified fragment, a distinctive ratio of charge/translational frictional drag. The amplified regions may be reporter-labeled during or after amplification.

Figure 12A:
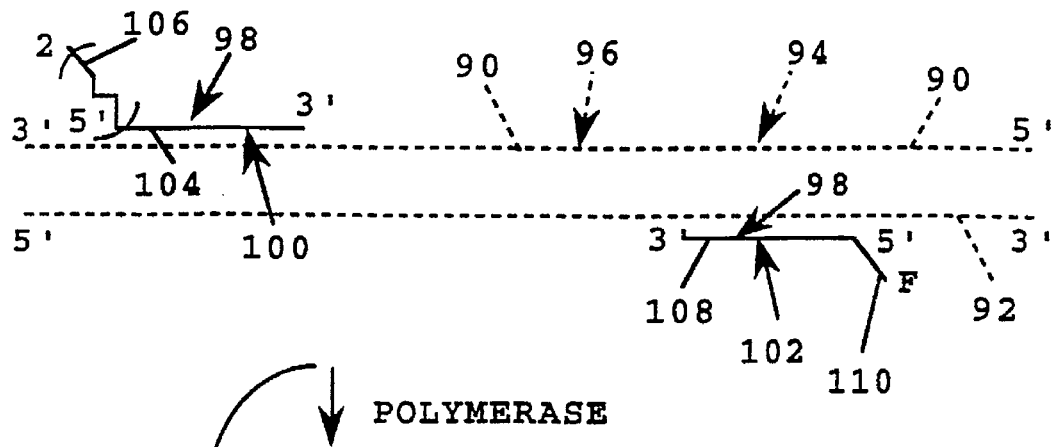
FIGS. 12A–12B illustrate the steps in a second embodiment of the invention, using palmer-initiated amplification to produce double-stranded labeled probes.
Figure 12B:
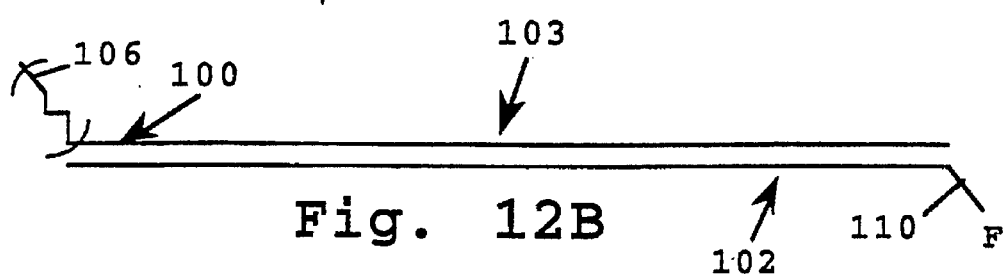

FIGS. 12A and 12B illustrate the method. The figure shows the two separate strands 90, 92 of a normally double-stranded target polynucleotide 94 having at least one, and typically a plurality of regions, such as region 96, to be amplified. The target is reacted with a probe composition whose probes each consist of a pair of palmer elements, such as elements 52, 54, in probe 50 described above with respect to FIG. 1C. FIG. 12A shows a probe 98 composed of polymer elements 100, 102. Polymer element 100 consists of an oligonucleotide polymer 104 designed for hybridization to a 3' end of one strand of region 96, which carries at its 5'-end, a selected-length polymer chain 106, similar to above-describe palmer element 52. Element 102 is an oligonucleotide palmer designed for hybridization to a 5' end of the opposite strand region 96, which carries a fluorescent reporter at its 5'-end.

In practicing this embodiment of the method, the probe composition is reacted with the target polynucleotide under hybridization conditions which favor annealing of the primer elements in the probe composition to complementary regions of opposite target polynucleotide strands, as illustrated in FIG. 12A. The reaction mixture is then thermal cycled through several, and typically about 20–40, rounds of primer extension, denaturation, primer/target sequence annealing, according to well-known polymerase chain reaction (PCR) methods (Mullis, Saiki). One amplified region, generated by the probe palmers 100, 102, is shown at 100 in FIG. 12B.

If, as in the example illustrated, one of the palmers is reporter-labeled, the double-stranded amplified region, such as region 103, forms a labeled probe having a polymer chain carried on one strand and a reporter on the other strand. Alternatively, the amplified sequences may be labeled in double-stranded form by addition of an intercalating or cross-linking dye, such as ethidium bromide. The different-sequence amplified probes can be fractionated in double-stranded form by electrophoresis as described above, based on the different ratios of charge/translational frictional drag of the double-stranded species.

The just-described method is useful, for example, in assaying for the presence of selected sequences in a target polynucleotide. As an example, the target polynucleotide may be genomic DNA with a number of possible linked gene sequences. The probes in the composition are polymer pairs effective in PCR amplification of the linked sequences of interest. After sequence amplification, the presence or absence of the sequences of interest can be determined from the electrophoretic migration positions of the labeled probes.

In another application, it may be desired to assay which of a number of possible primer sequences, e.g., degenerate sequences, is complementary to a gone sequence of interest. In this application, the probe composition is used to amplify a particular sequence. Since each primer sequence will have a distinctive polymer chain, the primer sequence complementary to the sequence end regions can be determined from the migration characteristics of labeled probes. As with the other applications discussed above, the method may involve including in the fractionated probe mixture, a series of oligonucleotides derivatized with polymer chains of known sizes, and labeled different reporters groups than are carried on the test probes, to provide migration-rate standards for the electrophoretic separation.

Figure 13A:
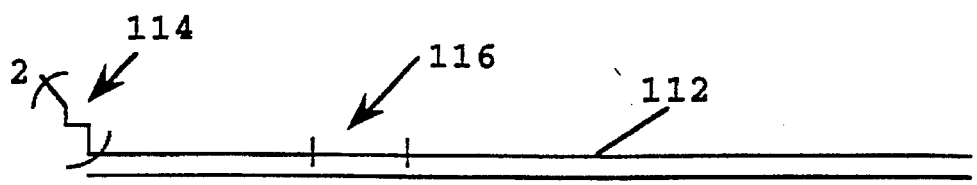
FIGS. 13A and 13B illustrate an alternative method for labeling amplified target sequences formed in the FIG. 12 method.
Figure 13B:
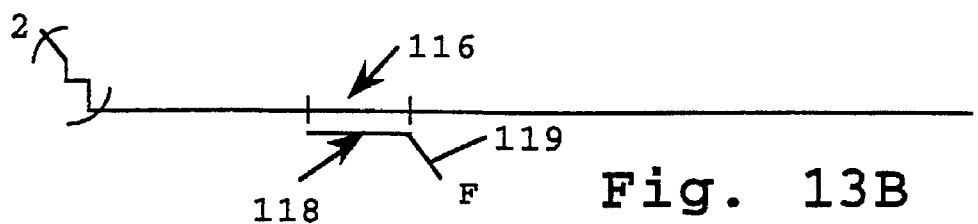

In still another application, the amplified target fragments are labeled by hybridizing to the amplified sequences, with such in single-stranded form, a reporter-labeled probe. This application is illustrated in FIGS. 13A and 13B, which show an amplified target sequence 112 having a polymer chain 114 carried on one strand. The aim of the assay is to determine whether any, and if so which, of the one or more fragments produced by the polymer probes contains a sequence complementary to the probe sequence. In this example, the fragment 112 contains a region 116 whose base sequence is complementary to that of a known-sequence probe 118.

The fragments, such as fragment 112, are hybridized with the one or more labeled probes under standard hybridization conditions, binding probe 118 to the strand of fragment 116 which contains the polymer chain, thus forming labeled probes which can be fractionated by electrophoresis, as above.

C. Probe Extension

Figure 14A:
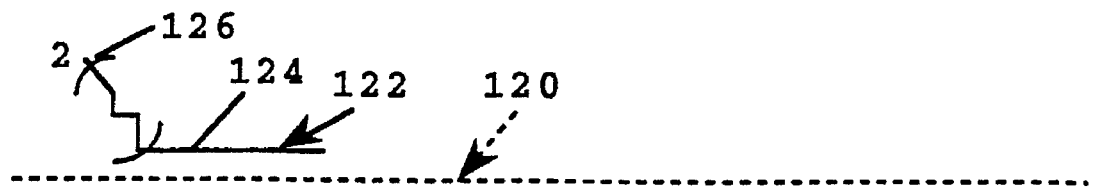
FIGS. 14A and 14B illustrate steps in a third general embodiment of the invention, using reporter-labeled nucleotide addition to the target-bound probes to form labeled probe species.
Figure 14B:
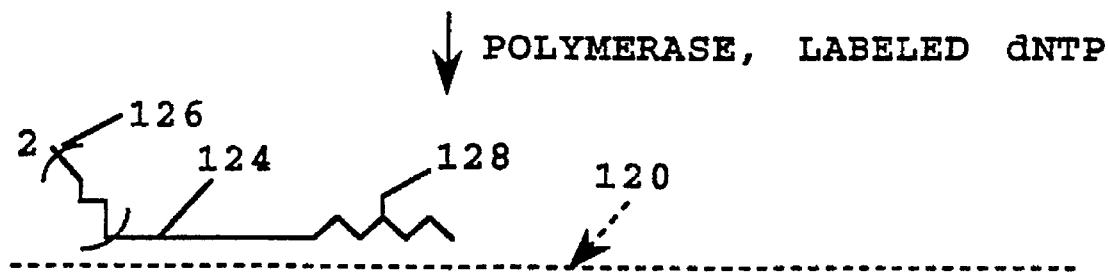

A third general method for forming labeled probes, in accordance with the method of the invention, is illustrated in FIGS. 14A and 14B. In this method, a single-stranded target polynucleotide, such as shown at 120 in the figures, is reacted with a probe composition containing a plurality of probes, such as probe 122 which are designed for base specific binding to selected regions of the target. Probe 12, which is representative, is like probe 20 in FIG. 1A, and includes an oligonucleotide having a free 3'-end OH group and a selected-length polymer chain carried at its 5' end.

After binding the probes to the target, the probes are treated with DNA polymerase in the presence of at least one reporter-labeled dNTP, as shown. Dye-labeled dNTPs can be synthesized from commercial starting materials. For example, amino 7-dUTP (Clontech. Palo Alto. Calif.) can be reacted with fluorescein NHS ester (Molecular Probes, Eugene, Oreg.) under standard coupling conditions to form a fluorescein-labeled dUTP. The polymerase is effective, in the presence of all four nucleoside triphosphates, to extend the 3' end of target-bound probes, incorporating one or more labeled nucleotides, as indicated at 128 to form the desired labeled probes having polymer chains which are characteristic of each profile sequence. Alternatively, in the above example, fluorescein may be coupled to the modified nucleotide, e.g., amino-7-dU, after incorporation into the probe.

After probe extension, the probes are released from the target and fractionated by electrophoresis, as above, to identify the migration positions of labeled probes corresponding to sequences contained in the target nucleotide.

D. Fragment Cleavage

Figure 17A:
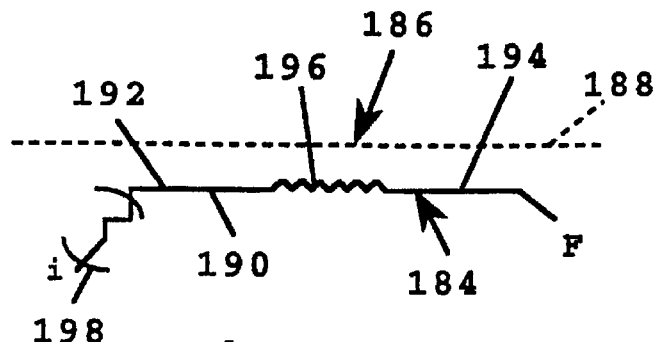
FIGS. 17A and 17B illustrate an alternative method for forming modified, labeled probes, in accordance with another embodiment of the invention.
Figure 17B:
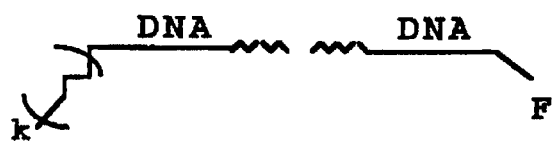

FIGS. 17A and 17B illustrate another embodiment of the method of the invention. In this method, the probe composition includes a plurality of sequence-specific probes, such as probe 184, designed for sequence specific binding to regions of a single-stranded target polynucleotide, such as region 186 in target polynucleotide 188. Probe 184, which is representative, includes a probe a binding polymer 190 composed of a first single-stranded DNA segment 192, and a second segment 194 which includes single-stranded RNA region 196. A polymer chain 198 attached to the binding polymers first segment imparts to the binding polymer, a distinctive charge/translational fraction drag ratio, as discussed above. A reporter 200 is attached to the second second segment of the binding polymer. In particular, the polymer chain and reporter are on opposite sides of the RNA region, so that selective cleavage in this region will separate the probes first segment and attached polymer chain from the reporter.

In the method, the probe composition is reacted with the target polynucleotide under hybridizatioon conditions, as above, to bind the probes in a sequence specific manner to complementary target regions. As seen in FIG. 18A, this produces a region of RNA/DNA duplex in each bound probe. The reaction mixture is now treated with a nuclease, such as RNase H, which is able to cut duplex RNA/DNA selectively, thus cutting each probe in its RNA binding region.

The hybridization reaction is now denatured, releasing, for each specifically bound probe, a modified labeled probe which lacks its polymer chain and thus now migrates as a free oligonucleotide by electrophoresis in a non-sieving medium. In an alternative embodiment (not shown), the polymer chain may be attached to reporter side of the probe, so that RNAse treatment releases a portion of the binding polymer, modifying the combined charge/combined translational frictional drag of the remaining probe (which contains the polymer chain and reporter), thus shifting the electrophoretic mobility of the probe in a nonsieiving medium, with respect to the uncleaved probe.

E. Fragment Modification

In a more general aspect, the invention provides a method of separating, on the basis of base sequence, oligonucleotide fragments having different base sequences. The method includes modifying the fragments, in a base-specific manner, to include (i) a selected-length, non-oligonucleotide polymer chain which imparts to each different-sequence fragment, a distinctive ratio of charge/translational frictional drag, and (ii) a detectable reporter, and fractionating the modified fragment(s) by electrophoresis.

In the ligated-probe method described above, fragments to be modified are the reporter-labeled probe elements, and the modification involves ligating onto the labeled probe elements another probe element having a polymer chain whose length is specific for each different-sequence labeled probe element.

In the primer-amplification method, the fragments to be modified are oligonucleotide sequences which are used to pdme polymerase extension and are amplified under conditions in which one strand is derivatized with a sequence-specific polymer chain and the other strand, with a reporter.

In the probe-extension method, the fragments to be modified are probes derivatized with selected-length polymer chains, where reporter addition to the probe occurs in those probes which are capable of binding to a known target sequence.

Figure 15A:
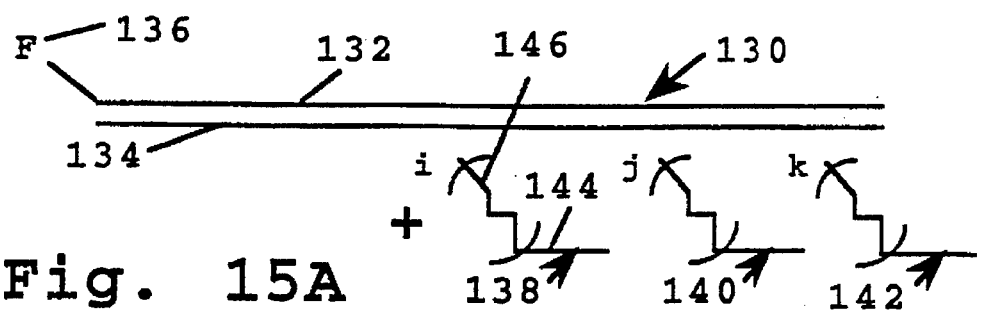
FIGS. 15A and 15B illustrate another method of modifying known-sequence polynucleotide fragments, in accordance with the method of the invention.
Figure 15B:
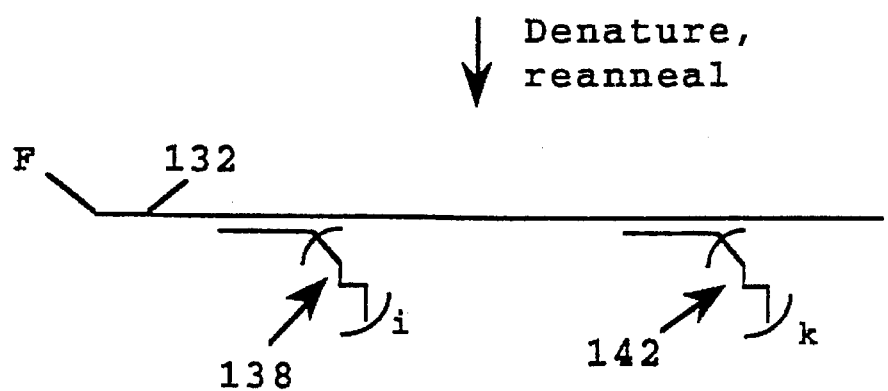

The method illustrated in FIG. 15A and 15B illustrates another method for modifying sequences in accordance with the method. In this embodiment, each fragment is a single- or double-stranded DNA fragment, such as double-stranded fragment 130 composed of strands 132, 136. In the embodiment illustrated, strand 132 has been fluorescent-labeled with a reporter 134 at one fragment end. The fragment strand can be reporter labeled by a variety of methods, such as by nick translation or homopolymer tailing in the presence of labeled dNTP's, or by PCR amplification using a reporter-labeled primer.

The fragments, which collectively include the target sequences in the method, are mixed with a probe composition that includes a plurality of probes, such as probes 138, 140, 142, designed for sequence-specific binding to different-sequence regions of one strand of the target. Probe 138, which is representative, includes an oligonucleotide 144 having the desired region-specific base sequence, and a polymer chain 146 which imparts to each different-sequence probe, a distinctive ratio of charge/fractional drag.

In the method, the fragments are modified by hytaddization, in single-stranded form, with the probes in the probe composition, forming fragments, such as fragment 150, with one or more double-stranded regions corresponding to probe binding. The modified fragments are reporter labeled in one strand and derivatized with one or more selected-length polymer chains in opposite strand probes.

The modified fragments are then fractionated in double-stranded form electrophoresis, to fractionate the fragments according to the number and size of polymer chains associated with each fragment.

Thus, for example, in the method illustrated, the fragment 132 binds probes 138, 142, and thus has been modified to carry a total of i+k polymer chain units. Since the fragments will migrate, on electrophoresis, with migration times which are dependent on the total number of polymer chain units attached to the fragments, the probe(s) associated with each fragment can be identified. This method can be used, for example to examine the distance between known sequences within genomic DNA, or for identifying linked sequences.

Figure 16A:
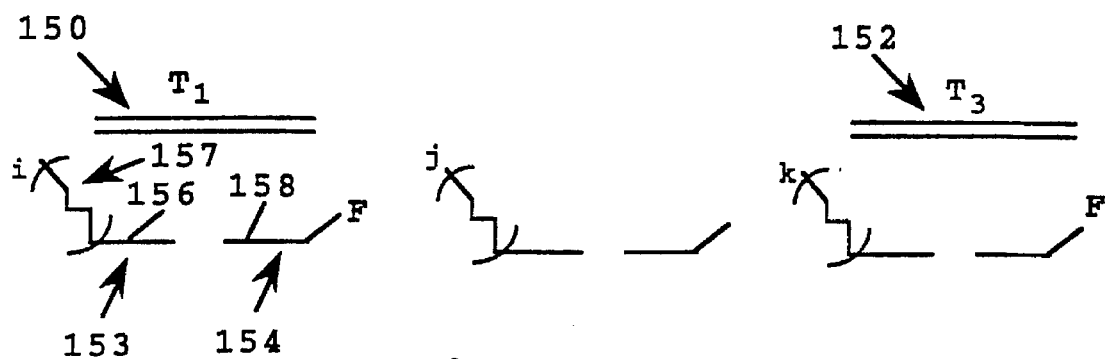
FIGS. 16A–16C illustrate an alternative method for forming modified, labeled probes, in accordance with the method of the invention.
Figure 16B:
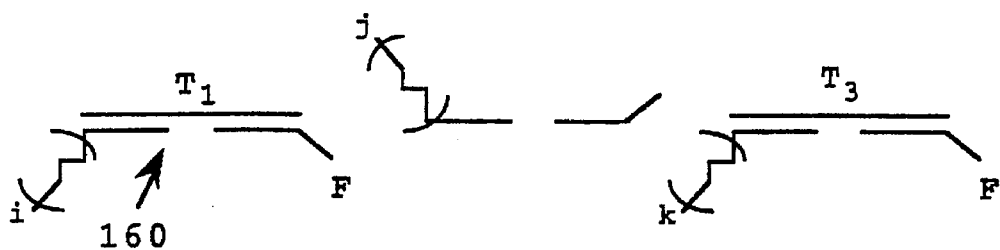
Figure 16C:
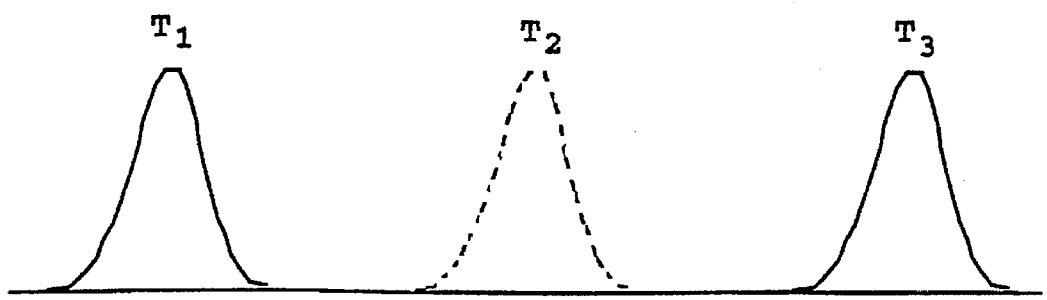

FIGS. 16A–16B illustrates another method for modifying polynucleotide fragments, in accordance with the invention. The method here is used to detect the presence of one or more sequences $S_1$ to $S_n$ associated with fragments $T_1$ to $T_n$, such as double-stranded fragments $T_1$ and $T_3$ shown at 150, 152, respectively. The fragments are modified in this method by hybridizing with a probe composition which includes, for each target sequence of interest, a pair of probe elements, such as probe elements 152, 154 which have the general construction of the probe elements described in FIG. 1B. That is, the element 152 includes an oligonucleotide 156 designed for base specific binding to one region of fragment $T_1$, and a selected length polymer chain 157, and element 154 is a reporter-labeled oligonucleotide 158 designed for base-specific binding to a second region of the fragment.

In the method, the fragments are modified by hybridization, in single-stranded form, with the probe elements in the probe composition forming fragments, such as fragment 160, with one probe having a selected-length polymer chain and a second reporter-labeled probe. The target fragment may be thought of in this method as serving a probe-ligating function to join the two probe elements. Since the fragment itself does appreciably change the electrophoretic mobility of the joined probe elements, when fractionated by electrophoresis, the method allows for identification of target sequence fragments according to the distinctive ratio of charge/frictional drag imparted by the polymer chain in one of the probe elements.

From the foregoing, it will be appreciated how various objects and features of the invention are met. The method allows a plurality of target sequences to be assayed in a single-format assay, with rapid identification of sequences according to the migration distances (migration rates) of different-length polymer chains associated with sequence-specific labeled probes.

The polymer chains allow for separation of charged binding molecules, such as oligonucleotides, in a simple electrophoresis method which does not require a sieving matrix. In particular, this CE fractionation method allows for effective fractionation of a plurality of oligonucleotides, all of which have similar or identical sizes. One advantage of this feature is that the plural probes used in the method can all have similar or the same sizes, and thus can be hybridized with target sequences with about the same hybridization kinetics and thermodynamics $(T_m)$.

The probes of the invention can be readily synthesized by conventional solid-phase methods. In one method, a polymer chain of a selected number of units can be formed directly on an oligonucleotide, by conventional solid-phase synthesis methods.

In an important embodiment of the invention, DNA sequencing is implemented by electrophoretically separating DNA fragments in a non-sieving liquid medium. Native DNA consists of two linear polymers, or strands of nucleotides. Each strand is a chain of nucleotides linked by phosphodiester bonds. The two strands are held together in an antiparallel orientation by hydrogen bonds between complementary bases of the nucleotides of the two strands: deoxyadenosine (A) pairs with thymidine (T) and deoxyguanosine (G) pairs with deoxycytidine (C). Presently there are two basic approaches to DNA sequence determination: the dideoxy chain termination method, e.g. Sanger et al, *Proc. Natl. Acad. Sci.,* Vol. 74, pgs. 5463–5467 (1977); and the chemical degradation method, e.g. Maxam et al, *Proc. Natl. Acad. Sci.,* Vol. 74, 560–564 (1977). The chain termination method has been improved in several ways, and serves as the basis for all currently available automated DNA sequencing machines, e.g. Sanger et al, *J. Mol. Biol.,* Vol. 143. pgs. 161–178 (1980); Schreier et al, *J. Mol. Biol., Vol.* 129, pgs. 169–172 (1979); Mills et al, *Proc. Natl. Acad. Sci.,* Vol. 76, pgs. 2232–2235 (1979); Smith et al, *Nucleic Acids Research,* Vol. 13, pgs. 2399–2412 (1985); Smith et al, *Nature,* Vol. 321, pgs. 5674–679 (1987); Prober et al, *Science,* Vol. 238, pgs. 336–341 (1987), Section II, *Meth. Enzymol.* Vol. 155, pgs. 51–334 (1987); Church et al, *Science,* Vol 240, pgs. 185–188 (1988); Tabor et al, *Proc. Natl. Acad. Sci.,* Vol. 84, pgs. 4767–4771 (1987); Tabor et al, *Proc. Natl. Acad. Sci.,* Vol. 86, pgs. 4076–4080 (1989); Innis et al, *Proc. Natl. Acad. Sci.,* Vol. 85, pgs. 9436–9440 (1988); and Connell et al, *Biotechniques,* Vol. 5, pgs. 342–348 (1987).

Both the chain termination and chemical degradation methods require the generation of one or more sets of labeled DNA fragments, i.e. nested sets of DNA fragments, each having a common origin and each terminating with a known base. The set or sets of fragments must then be separated by size to obtain sequence information. In both methods, the DNA fragments are separated by high resolution gel electrophoresis. Usually, the DNA fragments are labelled by way of radioactive nucleoside triphosphate precursors or by way of fluorescent dyes.

As used herein the term "chain terminating nucleotide" refers to a nucleotide or analog thereof which prevents further Polynucleotide chain elongation, or extension, after it has been incorporated into a growing DNA chain by a nucleic acid polymerase. Usually, the chain terminating property of such nucleotides is due to the absence or modification of the 3' hydroxyl of the sugar moiety. Preferably, the chain-terminating nucleotides are 2',3'-dideoxynucleotides. As used herein the term "spectrally resolvable" in reference to a set of dyes means that the fluorescent emission bands of the dyes are sufficiently distinct, i.e. sufficiently nonoverlapping, that target substances to which the respective dyes are attached, e.g. polynucleotides, can be distinguished on the basis of the fluorescent signal generated by the respective dyes by standard photodetection systems, e.g. employing a system of band pass filters and photomultiplier tubes, or the like, as exemplified by the systems described in U.S. Pat. Nos. 4,230,558, 4,811,218, or the like, or in Wheeless et al, pgs. 21–76, in *Flow Cytometry: Instrumentation and Data Analysis* (Academic Press, New York, 1985).

The basic steps of the chain-termination approach to DNA sequencing are (1) providing an oligonucleotide polymer and a template nucleic acid containing, as a subsequence, a target nucleic acid whose sequence is to be determined, (2) hybridizing the oligonucleotide polymer to the template nucleic acid, (3) extending the primer with a nucleic acid polymerase, e.g. T7 DNA polymerase, Sequenase™, a reverse transcriptase, or the like, in a reaction mixture containing nucleoside triphosphate precursors and at least one chain terminating nucleotide to form a nested series of DNA fragment populations, such that every shorter DNA fragment is a subsequence of every longer DNA fragment and such that each DNA fragment of the same size terminates with the same chain-terminating nucleotide, (4) separating the DNA fragment populations according to size, and (5) identifying the chain-terminating nucleotide associated with each DNA fragment population. As used herein, the term "nucleoside triphosphate precursors" refers to deoxyadenosine triphosphate (ATP), deoxycytidine triphosphate (CTP), deoxyguanosine triphosphate (GTP), and thymidine triphosphate (TTP), or analogs thereof, such as deoxyinosine triphosphate (ITP), 7-deazadeoxyguanosine triphosphate, and the like. The details of each of the above steps varies according to several factors well known in the art, including the nature of the labelling means for identifying the different chain-terminating nucleotides, the means for separating the different DNA fragment populations, the manner in which the template nucleic add is provided for the hybridization step, and the like. For example, if the DNA fragment populations are identified by fluorescent dyes attached to primers, then four different primers are provided, each having a different fluorescent label, and the primers are extended in four separate reaction mixtures corresponding to the four different chain-terminating nucleotides. Or, if the DNA fragment populations are identified by the incorporation of radioactively labelled nucleoside triphosphate during the extension step, then the step of extending usually includes four separate reaction mixtures each containing a different chain-terminating nucleotide and the step of separating usually includes separating the DNA fragment populations of each reaction mixture separately according to size. Generally, the references cited in the second paragraph of the Background section disclose the steps of DNA sequencing and their important variations. Accordingly, these references are incorporated by reference.

Preferably, the different DNA fragment populations are identified by fluorescent dyes attached to the chain-terminating nucleotides. Accordingly, in the method of the invention a primer is extended by a DNA polymerase in a reaction mixture containing the four 1-thiotfiphosphate analogs of ATP, CTP, GTP, and TTP, and four chain-terminating nucleotides, each labelled with a different member of a set of spectrally resolvable fluorescent dyes, e.g. as disclosed by Fung et at, U.S. Pat. No. 4,855,225; Prober et al (cited above); or the like.

A template is provided in accordance with the teachings in the art, e.g. Technical Manual for Model 370A DNA Sequencer (Applied Biosystems, Inc., Foster City, Calif.). For example, the target sequence may be inserted into a suitable cloning vector, such as the replicative form of an M13 cloning vector, which is then propagated to amplify the number of copies of the target sequence. The single-stranded form of M13 is isolated for use as a template. Alternatively, a template can be provided by polyermerase chain reaction (PCR) as taught in the art, e.g. Innis et al, (cited above); Wilson et al, Biotechniques, Vol. 8, pgs. 184–189 (1990); Gyllensten, Biotechniques, Vol. 7, pgs. 700–708 (1989); and the like. After amplification, the template can be used in the polymerization reaction(s) either in liquid phase or attached to a solid phase support, e.g. as taught by Stahl et al, *Nucleic Acids Research,* Vol. 16, pgs. 3025–3038 (1988); Hultman et al, *Nucleic Acids Research,* Vol. 17, pgs. 4937–4946 (1989); or the like.

Primers for the method of the invention either can be synthesized on a commercial DNA synthesizer or can be purchased alone or as components in DNA amplification and/or sequencing kits, e.g. United States Biochemical Corporation (Cleveland, Ohio), Clontech (Palo Alto, Calif.) or the like. The step of hybridizing the polymer to the template is fully disclosed in the cited references, which provide detailed guidance for application to any particular embodiment of the present invention.

Kits of the invention generally comprise one or more polymers consisting of one or more oligonucleotides conjugated to a polymer chain. Preferably, the oligonucleotides of the primers are between 16 and 25 nucleosides in length. Preferably, kits of the invention further includes a nucleoside triphosphate precursor mix consists of the four nucleoside triphosphate precursors in a buffer. In one embodiment, the nucleoside triphosphate precusor mix may also include one or more chain terminating nucleotides. Alternatively, the chain terminating nucleotides may be separate components of the kit. Preferably, kits further include a nucleic acid polymerase and a reaction buffer for carrying out the polymerase reaction. Nucleic acid polymerases include DNA polymerases, RNA polymerases, and reverse transcriptase, and the like. Preferably, kits include a DNA polymerase, e.g. Taq polymerase, as disclosed by Gelfand, U.S. Pat. No. 4,889,818; or Sequenase, as disclosed by Tabor et al, U.S. Pat. No. 4,962,020; 4,795,699; 4,942,130; 4,994,372; and 4,921,794.

In one embodiment, kits include a single polymer and a dye-terminator mix as components. The dye-terminator mix contains the four chain-terminating nucleotides each labelled with a different fluorescent dye, preferably spectrally resolvable. Preferably, the chain-terminating nucleotides are dideoxynudeoside triphosphate. In one aspect of this embodiment, each dideoxynucteoside triphosphate is separately labelled with a dye selected from the set comprising 5- and 6-carboxyfluorescein, 5- and 6-carboxy-4,7-dichlorofluorescein, 2',7'-dimethoxy-5- and 6-carboxy-4,7-dichlorofluorescein, 2',7'- dimethoxy-4',5'-dichloro-5- and 6-carboxyfluorescein, 2',7'-dimethoxy-4',5'-dichloro-5- and 6-carboxy-4,7-dichlorofluorescein, 1', 2',7',8'-dibenzo-5- and 6-carboxy-4,7-trichlorofluoroescein, 1',2',7',8'-dibenzo-4',5'-dichloro-5- and 6-carboxy-4,7-dichlorofluorescein, 2',7'-dichloro-5-and 6-carboxy-4,7-dichlorofluorescein, and 2',4',5, 7,-tetrachloro-5- and 6-carboxy-4,7-dichlorofluorescein. The above-mentioned dyes are disclosed in the following references which are incorporated by reference: Hobb, Jr. U.S. Pat. No. 4,997,928; Fung et al, U.S. Pat. No. 4,855,225; and Menchen et al, PCT application US90/06608. Alternatively, dideoxynucleotides of the invention may be labelled with spectrally resolvable rhodamine dyes as taught by Bengot et al, PCT application US90/05565.

In an alternative embodiment, kits include four separate primers that are each labelled with a different, spectrally resolvable, fluorescent dye, e.g. as taught by Fung et al (cited above).

The following examples describe various aspects of making and using polymer-chain probes. The examples are intended to illustrate, but not limit the scope of the invention.

Materials

Hexaethylene glycol, 4,4'-dimethoxytdtyl chloride, triethylamine, diisopropylethylamine, acetic acid, pyridine, methanesulfonyl chloride, sodium hydride, 2-cyanoethyl-N,N,N',N'-tetraisopropylphosphorodiamidite were obtained from Aldrich, Milwaukee, Wis., Diisopropylamine tetrazole salt, FAM-NHS/DMSO JOE-NHS/DMSO and TAMRA-NHS/DMSO were obtained from Applied Biosystems (ABi), Foster City, Calif. LAN (Linker Arm Nucleotide) 5'-dimethoxyl-tntyl-5-(N-(7-triuoroacetylaminoheptyl)-3-acrylamide)-2'-deoxyuridine-3'-phosphorami was obtained from Molecular Biosystems, Inc., San Diego, Calif.

Sephadex G-25M PD-10 columns were obtained from Pharmacia, Uppsala, Sweden. Derivatized oligonucleotides were LC purified using an ABI RP-300 (C8) column (4.6_ 220 mm) using a flow rate of 1.5 ml/min and a gradient of 0.1 M triethylammoniumacetateANater pH 7.0 and acetonitrile.

DNA synthesizer: 380B, ABI, Foster City, Calif.

EXAMPLE 1

Synthesis of $(HEO)_N$ Chains

The reactions described in this example are illustrated in FIG. 2 and are similar to Cload and Schepartz.

A. Dimethoxytrityl (DMT)-protected hexaethylene oxide (HEO)

27.0 gm (95.6 mmol) of HEO was dissolved in 100 ml pyridine. To this solution at room temperature was added a solution of 27.0 gm (79.7 mmol) of dimethoxytrityl chloride in 150 ml pyridine over 10 hr. The reaction was stirred at room temperature overnight (15 hr.) The solvent was removed in vacuo and the residue was brought up in 150 ml EtOAc and 100 ml $H_2O$, 2_100 ml brine and the organic layer was dried over $Na_2SO_4$. The solvent was removed to give a dark orange oil (38.36 gm). The crude material was purified by silica gel chromatography using 200 gm kiesel gel 60 and eluding with 2% methanolmethylene chloride (silica gel was basified with triethylamine). Appropriate fractions were combined to give 29.52 gm (50.49 mmol) of compound 1. Analysis of the DMT-protected HEO (compound 1 in FIG. 2) showed:

$^1$HNMR (300 MHz $CDCl_3$)$_{-7.5-68.8}$ (mult., 13H aromatic), 3.75 (S, 6H, $OCH_3$), 3.6 (20H, mult., $OCH_2$—$CH_2O$), 3.5 (2H, mult., $CH_2$—OH), 3.2 (2H, t, $CH_2ODMT$).

B. DMT-Protect HEO Phosphoramidite 1 gm (1.7 mmol) of DMT-protected HEO from Example 1A above and 0.029 g (0.17 mmol) of tetrazole diisopropyl ammonium salt were dissolved in 10 ml methylene chloride under inert atmosphere. To this was added 0.59 gm of 2-cyanoethyl tetraisopropyl phosphordiamidite, and the mixture was stirred overnight at room temperature. The reaction mixture was washed with a saturated solution of $NaHCO_3$, brine and dried over $Na_2SO_4$. The solvent was removed to give 1.58 gm crude oil, and the product was purified by flash chromatography through silica gel and eluded with 50% EtOAc-hexane (silica gel was basified with tdethylamine). 0.8 gm (1.3 mmol) of purified phosphoramidite (compound 2 in FIG. 2) was recovered.

C. DMT-protected HEO methanesulfonate (mesylate)

In 100 ml methylene chloride was dissolved 10.4 gm (17.8 mmol) of DMT-protected HEO from Example 1A above. The solution was ice cooled and 4.59 gm (35.6 mmol) of diisopropylethylamine was added, followed by the addition of 2.06 g (26.7 mmol) methanesulfonyl chloride. The reaction mixture was stirred for 30 minutes and then washed with a saturated solution of $NaHCO_3$, brine and dried over $Na_2SO_4$. The solvent was removed in vacuo to give 11.93 gm of the mesylate (compound 3 in FIG. 2).

D. DMT-protected HEO dimer

To a suspension of 0.62 gm (26.9 mmol) of sodium hydride in 150 ml freshly distilled tetrahydrofuran at 10_C was added 10.14 gm (36.0 mmol) of hexaethylene glycol over 1 minute, and the mixture was stirred for at room temperature for 30 minutes. To this was added a solution of 11.93 gm (17.9 mmol) of HEO mesylate from Example 1C above in 50 ml tetrahydrofuran. The reaction mixture was warmed to 40–50_C for 3 hours, after which the solvent was removed in vacuo and the residue was brought up in 150 ml of methylene chloride. This was washed with 3_100 ml H₂O, brine and dried over Na₂SO₄. The solvent was removed in vacuo to give a crude oil (13.37 gm), which was purified by silica gel chromatography as in Example 1A above. 10.0 gm of the DMT-protected HEO dimer (11.8 mmol) was recovered. Analysis of the material (compound 4 in FIG. 2) showed:

$^1$HNMR (300 MHz CDCl₃)__7.5–6.8 (mult., 13H aromatic), 3.75 (S, 6H, OCH₃), 3.6 (20H, mult.. OCH₂—CH₂O), 3.5 (2H. mult., CH₂—OH), 3.2 (2H, t, CH₂ODMT).

E. Phosphoramidite of the DMT-protected HEO dimer (Compound 5 in FIG. 2).

1 gm (1.17 mmol) of DMT-protected HEO dimer from Example 1D and 20 mg (0.12 mmol) of tetrazole diisopropyl ammonium salt were dissolved in 10 ml methylene chloride under inert atmosphere. To this at room temperature was added 0.409 gm (1.35 mmol) of 2-cyanoethyl tetraisopropyl phosphordiamidite. After 15 hr., the reaction was washed with saturated NaHCO₃, brine and dded over Na₂SO₄. The solvent was removed in vacuo to give crude oil (1.44 gm), which was purified by flash chromatography as in Example 1B. 0.76 gm (0.73 mmol) of purified product was recovered. Analysis of the purified material (compound 5 in FIG. 2) showed:

$^{31}$P—NMR (CD₃CN, H decoupled):__151 (s).

EXAMPLE 2

Synthesis of (HEO)$_N$ Chains linked by Bisurethane tolyl Groups

Figure 3A:
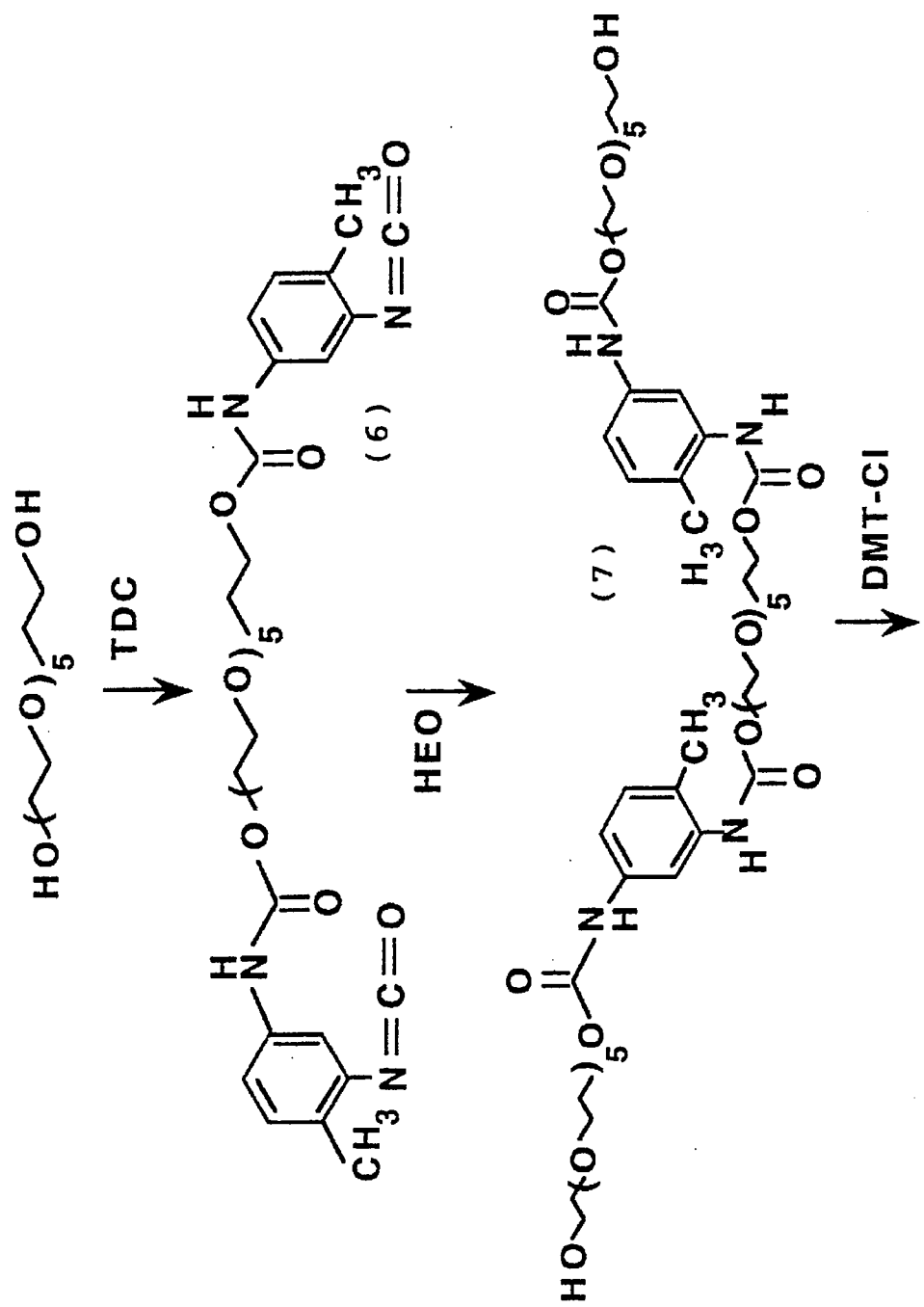
FIG. 3A and 3B illustrate methods of synthesis of polyethylene glycol polymer chains in which HEO units are linked by bisurethane tolyl linkages.
Figure 3B:
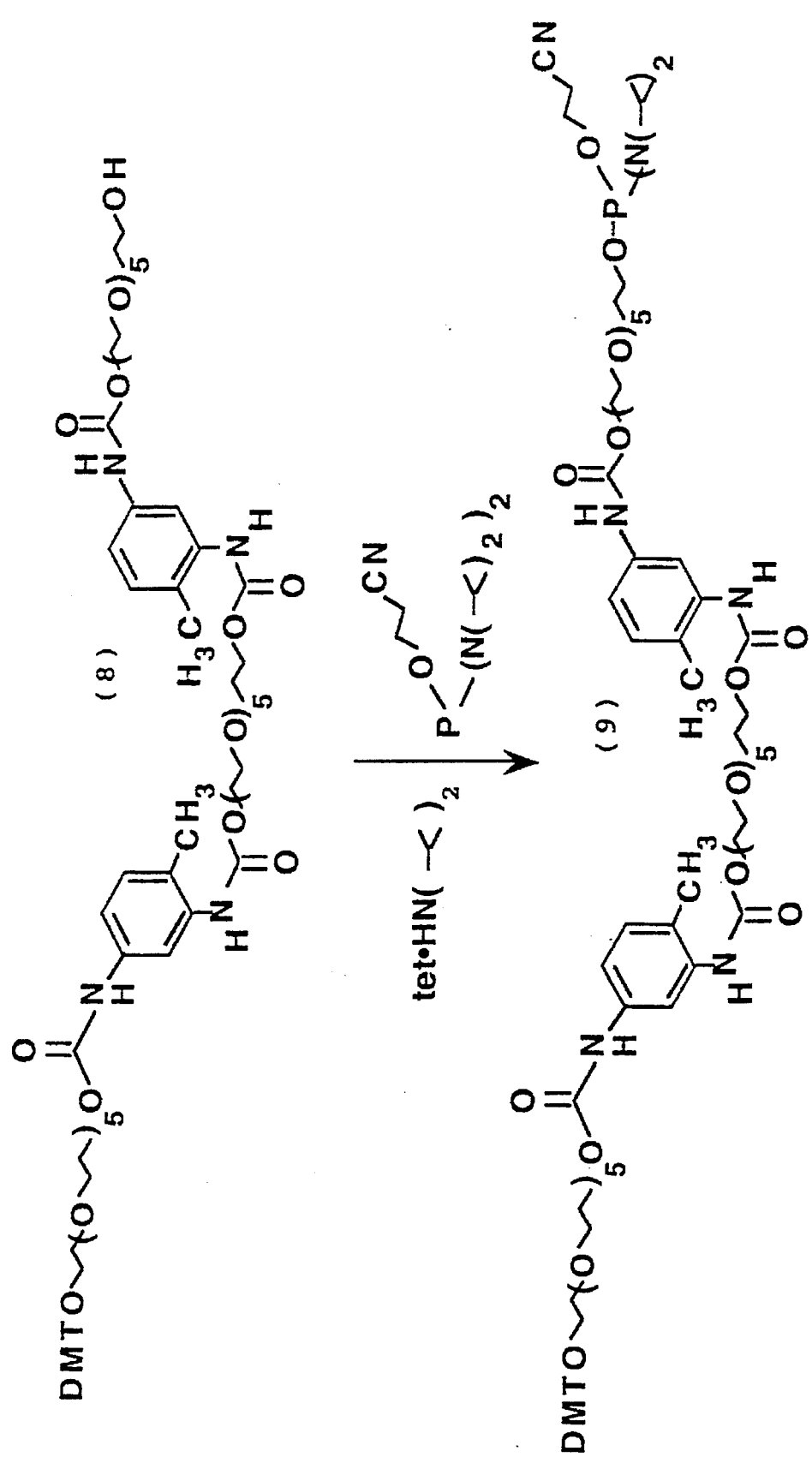

The reactions described in this Example are illustrated in FIGS. 3A and 3B.

Hexaethylene glycol (10.0 ml) was added dropwise to tolylene-2,4-diisocyanate (TDC) (17.0 ml) under argon at 30–35__C. An ice bath was used to control the exothermic reaction. The reaction was allowed to stand at room temperature overnight; washed with hot hexane (10×) to remove excess diisocyanate; and concentrated under reduced pressure to yield the crude bisisocyanate product (compound 6, FIG. 3A) as an amber oil (30 g).

A solution of the above crude bisisocyanate (2.3 g) and hexaethylene glycol (7.0 ml) in dichloromethane (25 ml) was stiffed at room temperature for 1 hour and then dibutyltindilaurate (0.1 ml, Aldrich) was added and stirred at room temperature for 22 hours; diluted with dichloromethane and washed with water (4__20 ml); dried (MgSO₄); and concentrated under reduced pressure to give the crude diol product (compound 7, FIG. 3A) as an amber oil (4.6 g).

A solution of DMT chloride (1.2 g) in dichloromethane (20 ml) was added dropwise over 2 hours under argon at room temperature to a stirred solution of the above crude diol (4.4 g) and triethylamine (0.6 ml, Aldrich) in dichloromethane (25 ml). The reaction solution was stirred at room temperature for 2 hours and washed with water, added (MgSO₄); and concentrated under reduced pressure to give the crude DMT alcohol product as an amber oil (5.1 g). Column chromatography (triethylamine neutralized silica, 5% methanol/dichloromethane) of the crude DMT alcohol gave the purified DMT alcohol (compound 8, FIG. 3B) as a viscous amber oil (0.72 g). Analysis of the compound showed: 1H NMR/CDCl₃:__6.7–7.5 (m, ArH, 19H),__4.3 (m, NC(O)OCH₂, 8H). __3.77 (s, CH₃O, 6H), 3.55–3.75 (m. CH₂OCH₂, 62H), __3.2 (t, DMTOCH2, 2H), __2.15 (m, CH₃Ar, 6H).

2-Cyanoethyl-N,N,N-N-tetraisopropylphosphorediamidite (0.20 ml) was added under argon at room temperature to a stiffed solution of the above purified DMT alcohol and tetrazole-diisopropylamine salt (12 mg) in dry dichloromethane (5 ml). After stirring at room temperature for 4 hours, NaHCO₃ solution as added and stirred for 40 minutes. The dichloromethane layer was diluted with more dichloromethane and washed with brine; dried (MgSO₄); and concentrated under reduced pressure to give the crude phosphoramidite product (compound 9, FIG. 2) as an amber oil (0.88 g). $^{31}$P NMR (CDCl₃): 151 ppm.

EXAMPLE 3

Derivatization of Oligonucteotides with PEO Chains

The reactions described in Sections B and C are illustrated in FIGS. 4A and 4B, respectively.

A. Preparation of Oligonucleotide

A 48-base oligonucleotide having the sequence

5'GCACCATTAAAGAAAATATCATCTTTG-GTGTTTCCTATGATGAATATA (SEQ. ID. NO.:1) carboxyfluorescein-3' (composition 10 in FIG. 4A) was prepared using a 3'-linked carboxyfluorescein polystyrene support (Applied Biosystems, Inc.) or can be prepared using 3'-Amine-ON (oligonucleotide) CPG (Ciontech, Palo Alto, Calif.) and FAM-NHS (ABI) according to published methods (Applied Biosystems, Caruthers, Connell) and standard phosphoramidite chemistry on an Applied Biosystems 380B DNA Synthesizer.

B. Oligonucleotide Derivatized with PEO Chain

The support-bound oligonucleotide from Example 3A above 0.1 __mol oligonucleotide was deprotected by reaction with trichloroacetic acid, washed, then reacted with one of the phosphoramidite-PEO polymers as in Example 1, using a standard DNA synthesis cycle. The embodiment shown in FIG. 4A is with polymer chain with 12 ethylene oxide subunits. The derivatized oligonucleotide (Compound 11 in FIG. 4A) was cleaved off the column with trityl on, and the collected product (compound 12 in FIG. 4A) was purified by liquid chromatography, using an ABI RP-300 (C-8) 4.6×220 mm column and a 0.1M triethylammonium acetate-water and acetonitrile solvent system. The derivatized oligonucleotide is shown as compound 12 in FIG. 4A.

C. Oligonucleotide derivatized with bisurethane tolyl-linked PEO Chain.

The support-bound oligonucleotide from Example 3A above (0.1 __mmol oligonucleotide) (Compound 10, FIG. 4B) was reacted with a phosphoramidite-PEO bisurethane tolyl-linked polymer prepared as in Example 2 using a standard DNA synthesis cycle. (The tolyl-linked polymer indicated by subunit stucture T-HEO-T-HEO in FIG. 4B corresponds to Compound 7 (in FIG. 3A). The derivatized oligonucleotide (Compound 13 in FIG. 4B) was cleaved off the column and deprotected with trityl on, and purified by liquid chromatography, using an ABI RD-300 (C-8) 4.6×220 mm column and a 0.1M triethylammonium acetate-water and acetonitrile solvent system. The collected product was deprotected with acetic acid. The derivatized oligonucteotide is shown as compound 14 in FIG. 4B.

EXAMPLE 4

Successive PEO Additions to an Oligonucleotide

The reaction steps described in this Example are illustrated in FIG. 5.

A. FAM-labeled Oligonucleotide

A 26 base oligonucleotide having the sequence 5' TTG GTG TTT CCT ATG ATG AAT ATA-LAN-T3' (SEQ. ID NO. :2) was made on an ABI model 380B DNA synthesizer using standard phosphoramidite chemistry (composition 15 in FIG. 5). LAN is a base modified deoxyuridine phosphoramidite (Molecular Biosystems Inc.) with a TFA protected amine. The 26 mer was made from a 1_m column using trityl on manual protocol after completion of synthesis. The column material was divided into 10 separate 0.1_mol columns.

All of the subsequent oligos were cleaved off the support with $NH_4OH$ and purified first by HPLC using an ABI RP-300 (C-8) column (4.6×220 mm) using a flow rate of 1.5 ml/min. and a solvent gradient of 0.1M triethylammonium acetate-water pH 7.0 and acetonitrile, then after the specific modifications described below, the trityl is removed and the product were isolated by HPLC using the conditions described above.

The cleaved oligonucleotides were labeled with FAM by adding a solution of the amine-labeled 26 mer with 15_1 of FAM_NHS in DMSO (ABI) and 40_1 of 1M $NaHCO_3$/$Na_2CO_3$ pH 9.0. After 2 hours the reaction mixtures were passed through a Pharrnada PD-10 Sephadex G25M column (Pharmacia) and the collected samples were then HPLC purified. After removal of the solvent the samples are dehydrated with 80% acetic add-water. The solvent was then removed in vacuo and the residue was brought up in 0.5 ml $H_2O$ and is LC purified.

B. FAM Labeled PEO-Derivatized Oligonucleotides

DMT-protected phosphoramidite HEO units from Example 1B were added to the 5' end of the oligo from Example 4A by standard phosphoramidite chemistry on solid support, yielding the composition 16 in FIG. 5. One to four units were added on in separate reactions. The resulting HEO modified oligos were cleaved from the solid support (Compound 17, FIG. 5) as above, and labeled with FAM and purified (Compound 18, FIG. 5), also as described above.

C. PEO-Derivatized Oligonucleotides

A 25 base oligonucleotide having the sequence 5'GGC ACC ATT AAA GAA AAT ATC ATC T 3' (SEQ. ID. NO. :3) was made as described in Example 4A. DMT-protected phosphoramidite HEO units were added to the 5' end of this 25 mer and purified as described in Example 4B.

EXAMPLE 5

Conjugation of a Peptide to an Oligonucleotide

A 25 mer oligonucleotide was synthesized on CPG solid support with an ABI DNA synthesizer. To the 5' hydroxyl of the CPG supported oligonucleotide was added N-MMT-$C_6$ Amino Modifier using standard phosphoramidite chemistry. This is a monomethoxytrityl protected amino linked phosphoramidite which is commercially available from Clontech Laboratories, Palo Alto, Calif., The monomethoxytdtyl group was removed using a standard trityl cleavage protocol on a DNA synthesizer and the DNA synthesis column was then placed on an ABI Peptide synthesizer capable of performing FMOC chemistry. Using standard FMOC peptide synthesis protocols, a four and an eight unit amino add peptide was conjugated onto the 5'-terminal amine of the CPG supported oligonucleotide. After completion of the synthesis, the terminal amine of the peptide was acetylated using a standard peptide capping protocol.

The synthesis column was then placed onto an ABI DNA synthesizer and the peptide-oligonucleotide was cleaved off the support and purified by HPLC using the conditions as previously described to produce the peptide-oligonucleotides Ac (Phe-Ala$_2$ or 4-NH(CH$_2$)$_6$-phosphate 5' GGC ACC ATT AAA GAA-AAT ATC ATC T-3'(SEQ ID. NO.:3). Ligation of the peptide-oligonucleotide to a fluorescent-labeled oligonucleotide in the presence of an oligonucleotide target was performed as described in Example 7A. CE analysis is shown in FIG. 9.

EXAMPLE 6

Capillary Electrophoretic Separation of Probes

Capillary electrophoresis (CE) was carried out using a CE breadboard including a laser-based detector. The systems includes a high-voltage power supply, a manual vacuum pump, and a PMT detector with a 530 nm RDF filter on the detected light. The laser was a 40 mW Ar ion laser. The capillary tube used in the system was a fused silica capillary tube 55 cm long with a 50 _m i.d. and 350 _m.

The grounded cathodic reservoir and the anedic reservoirs were filled with 75 mM tris-phosphate, pH 7.6, containing 8M urea.

A DNA mixture containing the four 26 mer oligonucieotides derivatized with 0,1,2, or 4 phosphate-linked HEO units, prepared as in Example 4, was diluted with 89 mM trisborate buffer, pH 7.6, to a final DNA concentration of about $10^{-8}$ M. About 2 nanoliters of the DNA solution was drawn into the cathodic end of the tube by electrokinetic injection.

The electrophoretic system was run at a voltage setting of about 15 kV (about 270 V/cm) throughout the run. Fluorescence detection was at 530 nm. The detector output signal was integrated and plotted on an HP Model 3396A integrator/plotter.

The electropherogram obtained is shown in FIG. 6. The numbers above the major peaks are electrophoresis times, in minutes. Total run time was about 22 minutes. The fastest-running peak, having a run time of 20.397 minutes, corresponds to the underivatized oligonucleotide. The oligonucleotides with 1, 2, and 4 HEO groups have migration peak times of 20.612, 20.994, and 21.559, respectively.

EXAMPLE 7

Template Bedred Probes and Electrophoretic Separation

A. Ligation of Probe Elements

A flint probe having the sequence 5' GGC ACC ATT AAA GAA AAT ATC ATC T-3'(SEQ I.D. NO:3) was derivatized with a either a tetrapeptide Phe-Ala-Phe-Ala, or an octapeptide Phe-Ala-Phe-Ala-Phe-Ala-Phe-Ala according to methods given in Example 5. A second probe having the sequence 5' P-TTG GTG TTT CCT ATG ATG AAT ATA G JOE 3'(SEQ ID. NO: 2) was prepared by standard methods.

The probes were targeted against a 48-base oligonucleotide representing the F508 region of the cystic fibrosis gene. Probe hybridization to the target and ligation of the hybridized probes was performed substantially as follows:

Peptide-derivatized oligonucleotide (50 nM, 20 _1), and the fluorescence-labeled oligonucleotide (50 nM, 20_1) were mixed with target oligonucleotide (50 nM, 20_1); salmon sperm DNA (4 ug/10_, 20 _1); 10× reaction buffer (200 mM Tris_HCl pH 7.1; 1M KCl; 100 mM MgCl$_2$; 100 mM dithiothreitol; 10 mM nicotinamide-adeninedinucletide) (20 1); ligase (30 units, 100 units/_1, Epicentre Technologies Ampligase, Madison, Wis.) and 100 _l of distilled water. The prepared sample was overlayed with 50 μl of oil and heated in a Perkin-Elmer Cetus DNA Thermal Cycler (Norwalk, Conn.) at 94_C for 3 minutes and then at 62_C for 60 minutes.

B. Capillary Electrophoretic Separation of Probes in a Non-Sieving Medium

A released ligated and non-ligated probe from above was ethanol precipitated and analyzed by CE electrophoresis in a non-sieving matrix. The capillary tube was a DB-5-coated capillary (J&W Scientific, Folsom, Calif.), 55 mm long, 40 mm to detector. The capillary was coated with a 0.5% surfactant solution prior to electrophoresis to render the capillary wall more hydrophilic. A variety of surfactants, such as BRIJ-, and TWEEN'-, jeffamine class surfactants, are available for this purpose.

A 10 _l sample, heated to 95_C for 2 minutes, was drawn into the tube. The buffer medium and electrophoresis medium was a 75 mM Tris-phosphate buffer, pH 8.0, 8M urea, 10% (v/v) MeOH. Electrophoretic run conditions were as described in Example 6. The electropherogram results are shown in FIG. 9, discussed above.

EXAMPLE 8

LCR Amplification and Separation of Ligated Probes

The following four probes were prepared:

(1) 5' GGC ACC ATT AAA GAA AAT ATC ATC T-3'(SEQ ID. NO.:3) derivatized at its 5' end with a either a 2 or 4 unit DEO (dodecyl ethylene oxide) polymer chains, according to synthetic methods described in Example 4, except in this case the units are 12 mers (2 or 4 12 mers) of ethylene oxide;

(2) 5' P-TTG GTG TTT CCT ATG ATG AAT ATA G 3'-JOE, (SEQ I.D. NO:2)prepared as in Example 7.

(3) 5' ROX-CTA TAT TCA TCA TAG GAA ACA CCA AA 3'-OH, (SEQ I.D. NO:4) prepared according to published methods (Applied Biosystems); and (4) 5'-P-GAT GAT ATT TTC TTT AAT GGT GCC-3' TAMRA (SEQ I.D. NO.:5) prepared with 3'-Amine-ON CPG, 5'-Phosphate-ON and Tamra-NH5 (ABI) using published methods (Applied Biosystems, Caruthers Connell).

Probes 1 and 2 are designed to span a portion of one strand of the F508 region of the cystic fibrosis gene, as in Example 8. Probes 3 and 4 are designed to span the same portion of the F508 region of the opposite strand of the gene. Ligase chain reaction was performed according to published methods (VVinn-Deen). HCl, LCR assays were carried out in 20 mmol/L Tris_HCL buffer. pH 7.6, containing 100 mmol of K$^+$, 10 mmol of Mg$^{2+}$, 10 mmol of dithiothreitol, 1 mL of Triton X-100, and 1 mmol of NAD$^+$ per liter. Each 100 _L of reaction mixture contained 1 pmol of each of the four oligonucieotides and 15 U of thermal-stable ligase (Epicentre Technologies, Madison, Wis.). To mimic the complexity of the human genome, we added 4 _g of heating sperm DNA to each reaction mixture. Reactions were carried out in 100_L aliquots overlayed with 100_L of mineral oil in Thin Walled Gene-Amp-, (Perkin-Elmer Cetus, Norwalk, Conn.) reaction tubes. All LCR reactions were run in a Perkin-Elmer Cetus model 9600 thermal cycler for 30 cycles of 94_C (10S) and 60_C (2 min). At the end of the cycling protocol, the reactions were cooled to 4_C.

The sample was ethanol precipitated and analyzed by CE electrophoresis in a nonsieving matrix. The capillary tube was a coated capillary, as in Example 7. A 10 _l sample, heated to 95_C for 2 minutes, was drawn into the tube. The buffer medium and electrophoresis medium was a 75 mM Tris-phosphate buffer, pH 8.0, 8 M urea, 10% (v/v) MeOH. Electrophoretic run conditions were as described in Example 7. The electropherogram results are shown in FIG. 11, discussed above.

EXAMPLE 9

DNA Sequencing in a Non-sieving Liquid Medium

DNA sequencing in accordance with the invention is carried out by providing binding polymer/polymer chain conjugates as sequencing palmers in the standard chain termination approach to DNA sequencing. Preferably, the same polymer chain is attached to each binding polymer to form polymers for sequencing. After annealing to a template strand of DNA, the polymers are extended with a polymerase in the presence of nucleoside triphosphate precursors and chain terminating nucleotide to form one or more sets of different sized DNA fragments, depending on whether palmers are labeled or chain terminators are labeled. The DNA fragments each have a common origin—the binding polymer, terminate with a known base, and are identically conjugated to the same polymer chain. The DNA fragments in each of the sets are then electrophoretically separated by size in a non-sieving liquid medium.

In this example, the following 47-mer synthetic potynucleotide is employed as a sequencing template.

5'-TCTATATTCATCATAGGAAACACCAATGATATT-TTCTTTAATGGTGC-3'(SEQ I.D. NO.:6)

The following primer having an 11-mer hexaethylene oxide polymer chain is synthesized as described in Examples 1–4:

5'-(HEO)$_{11}$-GCACCATTAAAGAAAATATCAT-3'(SEQ. I.D. NO.7)

Sequencing is carried out on an Applied Biosystems model 373 automated DNA sequencer using the manufacturers protocol for sequencing reactions using dye-labelled chain terminating nucleotides, with the following exception. Since the capillary separation apparatus of Example 7 is not configured for four color fluorescence measurements, four separate reactions are carried out: one for each of the four chain terminating nucleotides. After melting the extension products from the template in accordance with the manufacturer's protocol, the extension products of the four sequencing reactions are separately resolved by capillary electrophoresis as described in Example 7. As expected, two peaks are observed with the dideoxycytidine extension products, seven peaks are observed with the dideoxyadenosine extension products, ten peaks are observed with the dideoxythymidine extension products, and six peaks are observed with the dideoxyguanosine extension products.

Although the invention has been described with reference to various applications, methods, and compositions, it will be appreciated that various changes and modification may be made without departing from the invention.

What is claimed is:

1. In a method of determining the nucleotide sequence of a target nucleic acid, the method of the type wherein a nested set of DNA fragments produced by extension of an oligonucleotide primer are separated by size, an improvement comprising:

providing a nested set of DNA fragments, each DNA fragment of the set being conjugated to a polymer chain such that DNA fragments of different sizes have different ratios of charge to translational frictional drag in a non-sieving medium; and electrophoretically separating the DNA fragments in a non-sieving liquid medium.

2. The method of claim 1 wherein said step of providing a nested set of DNA fragments comprises the steps of:

providing a primer comprising an oligonucleotide conjugated to a polymer chain;

annealing the primer to the target nucleic acid; and extending the primer by a nucleic acid polymerase in the presence of nucleoside triphosphate precursors and at least one chain terminating nucleotide.

3. The method of claim 1 or 2 wherein the polymer chain is uncharged.

4. The method of claims 1 or 2 wherein the polymer chain has a neutral net charge.

5. In a method of determining the nucleotide sequence of a target nucleic acid, the method of the type wherein a nested set of DNA fragments produced by extension of an oligonucleotide primer are separated by size, an improvement comprising:

providing a nested set of DNA fragments, each DNA fragment of the set being conjugated to a polymer chain such that DNA fragments of different sizes have different electrophoretic mobilities in a non-sieving medium; and electrophoretically separating the DNA fragments in a non-sieving liquid medium.

6. A kit for determining the nucleotide sequence of a target nucleic acid comprising:

a primer, the primer having a polymer chain attached thereto, wherein the primer is extendible by a nucleic acid polymerase;

a nucleic acid polymerase; and nucleoside triphosphate precursors and at least one chain terminating nucleotide.

7. The kit of claim 6 wherein the chain terminating nucleotide is labeled with a fluorescent dye.

\* \* \* \* \*

SEQUENCE LISTING ( 1 ) GENERAL INFORMATION:

( i i i ) NUMBER OF SEQUENCES: 7

( 2 ) INFORMATION FOR SEQ ID NO: 1:

( i ) SEQUENCE CHARACTERISTICS:
        ( A ) LENGTH: 48 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO: 1:

```
GCACCATTAA AGAAAATATC ATCTTTGGTG TTTCCTATGA TGAATATA                48
```

( 2 ) INFORMATION FOR SEQ ID NO: 2:

( i ) SEQUENCE CHARACTERISTICS:
        ( A ) LENGTH: 25 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO: 2:

```
TTGGTGTTTC CTATGATGAA TATAG                                        25
```

( 2 ) INFORMATION FOR SEQ ID NO: 3:

( i ) SEQUENCE CHARACTERISTICS:
        ( A ) LENGTH: 25 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO: 3:

```
GGCACCATTA AAGAAAATAT CATCT                                        25
```

( 2 ) INFORMATION FOR SEQ ID NO: 4:

( i ) SEQUENCE CHARACTERISTICS:
        ( A ) LENGTH: 26 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO: 4:

```
CTATATTCAT CATAGGAAAC ACCAAA                                       26
```

( 2 ) INFORMATION FOR SEQ ID NO: 5:

( i ) SEQUENCE CHARACTERISTICS:
        ( A ) LENGTH: 24 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO: 5:

```
GATGATATTT TCTTTAATGG TGCC                                         24
```

( 2 ) INFORMATION FOR SEQ ID NO: 6:

( i ) SEQUENCE CHARACTERISTICS:
        ( A ) LENGTH: 47 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO: 6:

TCTATATTCA TCATAGGAAA CACCAATGAT ATTTTCTTTA ATGGTGC     47

( 2 ) INFORMATION FOR SEQ ID NO: 7:

( i ) SEQUENCE CHARACTERISTICS:
        ( A ) LENGTH: 22 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO: 7:

GCACCATTAA AGAAAATATC AT     22